United States Patent
Ke et al.

(10) Patent No.: US 10,466,259 B2
(45) Date of Patent: Nov. 5, 2019

(54) SYNTHETIC ANTIGEN COMPOSITIONS FOR DETECTING ANTI-PHOSPHATIDYLETHANOLAMINE ANTIBODIES

(71) Applicant: Northwestern Univeristy, Evanston, IL (US)

(72) Inventors: Ke Ke, Oak Ridge, TN (US); Songwang Hou, Wilmette, IL (US); Ming Zhao, Oak Park, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 87 days.

(21) Appl. No.: 15/349,368

(22) Filed: Nov. 11, 2016

(65) Prior Publication Data

US 2017/0138966 A1    May 18, 2017

Related U.S. Application Data

(60) Provisional application No. 62/254,518, filed on Nov. 12, 2015.

(51) Int. Cl.
| | |
|---|---|
| *G01N 33/92* | (2006.01) |
| *G01N 33/564* | (2006.01) |
| *A61K 31/685* | (2006.01) |
| *G01N 33/68* | (2006.01) |

(52) U.S. Cl.
CPC .......... *G01N 33/92* (2013.01); *A61K 31/685* (2013.01); *G01N 33/564* (2013.01); *G01N 2800/32* (2013.01); *G01N 2800/368* (2013.01)

(58) Field of Classification Search
CPC combination set(s) only.
See application file for complete search history.

(56) References Cited

PUBLICATIONS

Fager et al. A large-scale purification of phosphatidylethanolamine, lysophosphatidylethanolamine, and phophatidylcholine by high performance liquid chromatography: a partial resolution of molecular species. J. Lipid. Res. 1977, vol. 18, pp. 704-709 (Year: 1977).*
Small Changes of Dietary (n-6) and (n-3)/Fatty Acid Content Ratio Alter Phosphatidylethanolamine and Phosphatidylcholine Fatty Acid Composition During Development of Neuronal and Glial Cells in Rats. The Journal of Nutrition 1997, vol. 127, pp. 724-731. (Year: 1997).*
Bartlett, Phosphorus assay in column chromatography. J Biol Chem. Mar. 1959;234(3):466-8.
Berard et al., Antiphosphatidylethanolamine antibodies as the only antiphospholipid antibodies. I. Association with thrombosis and vascular cutaneous diseases. J Rheumatol. Aug. 1996;23(8):1369-74.
Boffa et al., Antiphosphatidylethanolamine antibodies as the only antiphospholipid antibodies detected by Elisa. II. Kininogen reactivity. J Rheumatol. Aug. 1996;23(8):1375-9.
Cullis et al., The polymorphic phase behaviour of phosphatidylethanolamines of natural and synthetic origin. A 31P NMR study. Biochim Biophys Acta. Oct. 19, 1978;513(1):31-42.
Drouvalakis et al., Microtitre plate and assay buffer alter detection of antiphosphatidylethanolamine antibodies in lupus anticoagulant positive plasma. Thromb Res. May 15, 1999;94(4):205-12.
Fundamental Immunology (1989) Ch. 7 Paul, W., ed., 2nd ed. Raven Press, N.Y.
Harper et al., X-ray diffraction structures of some phosphatidylethanolamine lamellar and inverted hexagonal phases. Biophys J. Nov. 2001;81(5):2693-706.
Harris, Syndrome of the black swan. Br J Rheumatol. Oct. 1987;26(5):324-6.
Hawke, The fatty acids of phosphatidylethanolamine and phosphatidylcholine from hen's egg. Biochem J. Mar. 1959;71(3):588-92.
Hudson et al., Engineered antibodies. Nat Med. Jan. 2003;9(1):129-34.
Karmochkine et al., Antiphosphatidylethanolamine antibody as the sole antiphospholipid antibody in systemic lupus erythematosus with thrombosis. Clin Exp Rheumatol. Nov.-Dec. 1992;10(6):603-5.
McIntyre et al., Anti-phosphatidylethanolamine (aPE) antibodies: a survey. J Autoimmun. Sep. 2000;15(2):185-93.
Miyakis et al., International consensus statement on an update of the classification criteria for definite antiphospholipid syndrome (APS). J Thromb Haemost. Feb. 2006;4(2):295-306.
Nayfe et al., Seronegative antiphospholipid syndrome. Rheumatology (Oxford). Aug. 2013;52(8):1358-67.
Rodriguez-Garcia et al., Clinical manifestations of antiphospholipid syndrome (APS) with and without antiphospholipid antibodies (the so-called 'seronegative APS'). Ann Rheum Dis. Feb. 2012;71(2):242-4.
Sanmarco et al., Antiphosphatidylethanolamine antibodies are associated with an increased odds ratio for thrombosis. A multicenter study with the participation of the European Forum on antiphospholipid antibodies. Thromb Haemost. Jun. 2007;97(6):949-54.
Sanmarco, Elisa for antiphosphatidylethanolamine antibody detection: high impact of assay buffer on results. J Immunol Methods. Jun. 30, 2010;358(1-2):9-16.
Staub et al., Antibody to phosphatidylethanolamine in a patient with lupus anticoagulant and thrombosis. Ann Rheum Dis. Feb. 1989;48(2):166-9.
Staub et al., Anti-phosphatidylethanolamine antibody, thromboembolic events and the antiphospholipid syndrome. Autoimmun Rev. Dec. 2012;12(2):230-4.
Sugi et al., Antiphosphatidylethanolamine antibodies in recurrent early pregnancy loss and mid-to-late pregnancy loss. J Obstet Gynaecol Res. Aug. 2004;30(4):326-32.

(Continued)

*Primary Examiner* — Shafiqul Haq
(74) *Attorney, Agent, or Firm* — Benesch, Friedlander, Coplan & Aronoff LLP

(57) ABSTRACT

Provided herein are compositions comprising distinct lipid species in defined ratios and methods of use thereof for the detection of anti-phosphatidylethanolamine (aPE) antibodies and diagnosis of antiphospholipid syndrome (APS).

10 Claims, 28 Drawing Sheets

(56) References Cited

PUBLICATIONS

Toombes et al., Determination of L(alpha)-H(II) phase transition temperature for 1,2-dioleoyl-sn-glycero-3-phosphatidylethanolamine. Biophys J. May 2002;82(5):2504-10.

Wilson et al., International consensus statement on preliminary classification criteria for definite antiphospholipid syndrome: report of an international workshop. Arthritis Rheum. Jul. 1999;42(7):1309-11.

* cited by examiner

SYNTHETIC ANTIGEN COMPOSITIONS FOR DETECTING ANTI-PHOSPHATIDYLETHANOLAMINE ANTIBODIES

CROSS REFERENCE TO RELATED APPLICATION

The present invention claims the priority benefit of U.S. Provisional Patent Application 62/254,518, filed Nov. 12, 2015, which is incorporated by reference in its entirety.

STATEMENT REGARDING FEDERAL FUNDING

This invention was made with government support under R01 HL102085 awarded by the National Institutes of Health. The government has certain rights in the invention.

FIELD

Provided herein are compositions comprising distinct lipid species in defined ratios and methods of use thereof for the detection of anti-phosphatidylethanolamine (aPE) antibodies and diagnosis of antiphospholipid syndrome (APS).

BACKGROUND

The clinical diagnosis of antiphospholipid syndrome (APS) requires the detection of the persistent presence of circulating antiphospholipid antibodies (aPL) in association with clinical symptoms such as vascular thrombosis and recurrent pregnancy losses. The laboratory criteria of aPL for the classification of APS include lupus anticoagulant (LA), anticardiolipin antibodies (aCL), and anti-β2-glycoprotein I antibodies (anti-β2GPI) (refs. 1-3; herein incorporated by reference in their entireties). However, in some instances, patients with clinical manifestations highly suggestive of APS lack any of the previously mentioned aPL (refs. 4-8; herein incorporated by reference in their entireties). These are referred to as seronegative APS. Accumulating evidence has shown that antibodies directed against phosphatidylethanolamine (PE) lipids, a class of lipids with zwitterionic PE head group, are strongly associated with similar or identical clinical symptoms of APS, in the absence of the laboratory criteria of this syndrome (refs. 9-11; herein incorporated by reference in their entireties). The investigation of anti-PE antibodies (aPEs) would impact the clinic diagnosis of unexplained thrombosis and recurrent pregnancy losses, therefore benefits the treatment outcome of APS.

ELISA is the most common assay for the detection of aPE in patient serum samples. However, there is currently no standardized aPE ELISA protocol, and a number of variations in aPE ELISA conditions have been reported in aPE literature. It has been shown that different sources of PE impact ELISA signals to some extent. Other variations in ELISA assay are attributed to the material of microplates, buffer systems and cofactor supplement used for aPE detection (refs. 12-15; herein incorporated by reference in their entireties). Altogether, prior studies reveal an inconsistent comparison among aPE detection data from different laboratories and raised a need for standardization of the assay.

SUMMARY

Provided herein are compositions comprising distinct lipid species in defined ratios and methods of use thereof for the detection of anti-phosphatidylethanolamine (aPE) antibodies and diagnosis of antiphospholipid syndrome (APS).

In some embodiments, provided herein are compositions formulated to contain defined quantities and/or ratios of specific PE species. In some embodiments, kits are provided comprising compositions having defined quantities and/or ratios of specific PE species. In some embodiments, such kits further comprise additional reagents and/or materials (e.g., multiwell plates) for performing immunoassays (e.g., ELISA assays (e.g., sandwich ELISA, competitive ELISA, etc.), etc.) using the defined-formulation PE-containing compositions described herein. In some embodiments, devices, such as conical tubes or multiwell plates, are provided that contain defined-formulation PE-containing reagents within said device (e.g., coated to a surface (e.g., an interior surface) thereof. In some embodiments, systems are provided comprising the defined-formulation PE-containing compositions described herein along with other components (e.g., buffers, secondary antibodies, labels, etc.), devices (e.g., multiwell plates), instruments (e.g., fluorimeters, etc.), etc. for the detection of aPA antibodies in a sample (e.g., blood sample from a subject). In some embodiments, methods are provided for using the compositions (e.g., comprising defined quantities and/or ratios of specific PE species), kits, devices, systems, etc., for example, to detect the binding of aPE antibodies in a sample (e.g., blood sample from a subject) to PE species in a defined-formulation PE-containing reagent.

In some embodiments, provided herein are compositions comprising a population of defined phosphatidylethanolamine (PE) species in known quantity and/or ratio. In some embodiments, compositions comprise two or more (e.g., 3, 4, 5, 6, 7, 8, 9, 10, or more, or ranges therebetween) distinct PE species. In some embodiments, compositions comprise at least one saturated PE species and at least one unsaturated PE species. In some embodiments, the at least one saturated PE species is selected from 16:0 PE and 18:0 PE. In some embodiments, compositions comprise 10-30% (e.g., 10%, 12%, 14%, 16%, 18%, 20%, 22%, 24%, 26%, 28%, 30%, or ranges therebetween) saturated PE. In some embodiments, compositions comprise two or more unsaturated PE species selected from the group consisting of myristoleic PE, palmitoleic PE, sapienic PE, oleic PE, elaidic PE, vaccenic PE, linoleic PE, linoelaidic PE, α-linolenic PE, arachidonic PE, eicosapentaenoic PE, erucic PE, and docosahexaenoic PE. In some embodiments, compositions comprise at least 10-30% (e.g., 10%, 12%, 14%, 16%, 18%, 20%, 22%, 24%, 26%, 28%, 30%, or ranges therebetween) of each of three distinct unsaturated PE species. In some embodiments, 20:4 PE is present in greater concentration than any other PE species. In some embodiments, compositions comprise at least 10-30% of each of 18:1 PE, 20:4 PE, and 22:6 PE. In some embodiments, compositions comprise 10-30% 18:0 PE, 5-20% 18:1 PE, 20-50% 20:4 PE, and 15-40% 22:6 PE. In some embodiments, compositions comprise about 20% 18:0 PE, about 13.3% 18:1, about 39.9% 20:4 PE, and about 26.6% 22:6 PE. In some embodiments, compositions provided herein outperform natural sources of PE (e.g., egg-derived PE) in immunoassays in terms of signal strength and/or signal consistency. In some embodiments, 18:1 PE comprises greater than 50% (e.g., 55%, 60%, 65%, 70%, 75%, 80%, 85%, 90%, 95%, 99%, 100%, or ranges therebetween) of the PE species in a composition.

In some embodiments, provided herein are methods comprising exposing a sample suspected of comprising anti-phosphatidylethanolamine (aPE) antibodies to the composition comprising a population of defined phosphatidylethanolamine (PE) species in known quantity and/or ratio, and detecting the binding of the aPE antibodies to the PE species to detect and/or quantify the aPE antibodies in the sample. In some embodiments, the sample is a blood sample from a subject and/or a processed blood product (e.g., plasma, serum, etc.). In some embodiments, the method comprises performing an enzyme linked immunosorbent assay (ELISA). In some embodiments, the ELISA is a sandwich ELISA or a competitive ELISA.

In some embodiments, provided herein are methods for diagnosing a subject with antiphospholipid syndrome (APS) comprising performing an immunoassay described herein on a biological sample from the subject.

In some embodiments, provided herein are systems comprising a vessel having a defined-formulation PE-containing reagent contained within and/or coated onto a surface of the vessel. In some embodiments, the vessel is a well of a multiwell plate, and the surface is a well-bottom and/or sidewall.

In some embodiments, provided herein are kits for performing an immunoassay, the kits comprising a defined-formulation PE-containing reagent and additional reagents and/or materials for performing the immunoassay, the additional reagents and/or materials selected from the group consisting of buffer, labeled secondary antibody, labeled aPE antibody, a microwell plate, software, and instructions.

PE, 67.5% 20:4 PE, and 0% 22:6 PE; 11, 10% 18:0 PE, 22.5% 18:1 PE, 0% 20:4 PE, and 67.5% 22:6 PE; 12, 10% 18:0 PE, 15% 18:1 PE, 75% 20:4 PE, and 0% 22:6 PE; 13, 10% 18:0 PE, 15% 18:1 PE, 0% 20:4 PE, and 75% 22:6 PE; 14, 10% 18:0 PE, 15% 18:1 PE, 30% 20:4 PE, and 45% 22:6 PE; 15, 10% 18:0 PE, 15% 18:1 PE, 45% 20:4 PE, and 30% 22:6 PE. 0.5 mg indicated PE was coated on each well of 96 plate, $OD_{405}$ was measured after Elisa and the relative OD value was deducted the normal human serum value and normalized with egg PE value. The error bar represents SEM. n=3. serum was from patient J083006H.

Figure 12A:
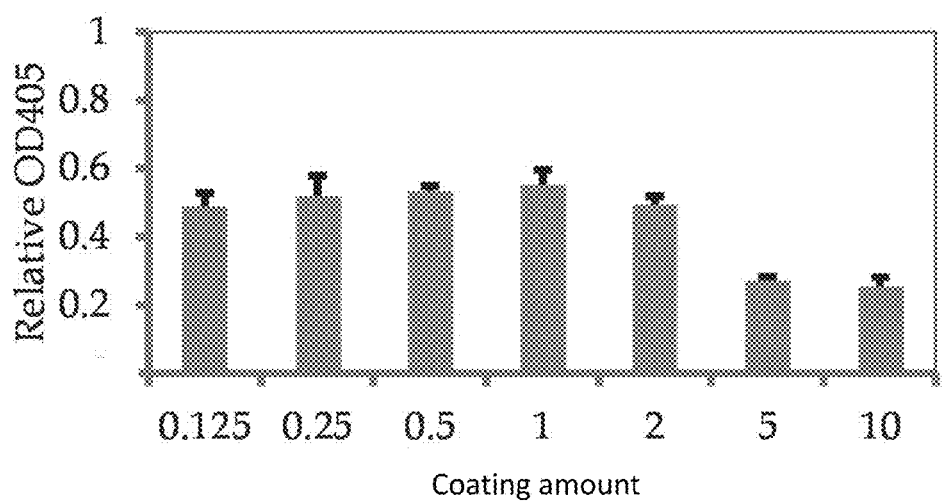
Figure 12B:
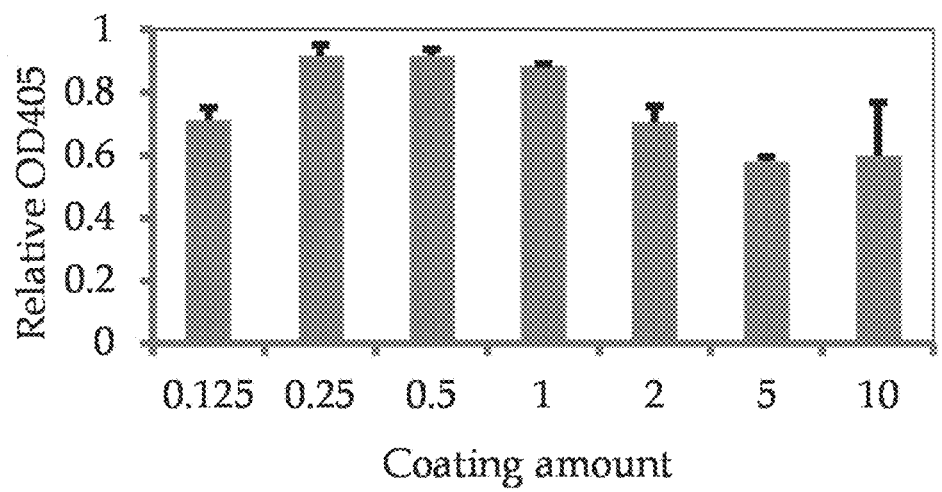

FIGS. 12A-B. Determination of PE coating amount and its impact on ELISA. A, B. determination of PE coating Amount. The indicated amount of PE was coated on 96 well plate and Elisa was performed. The relative $OD_{405}$ value was deducted the normal serum value. The error bar represents SEM, n=3. A for egg PE, B for 20% 18:0 PE, 13.3% 18:1 PE, 39.9% 20:4 PE, and 26.6% 22:6 PE.

Figure 13:
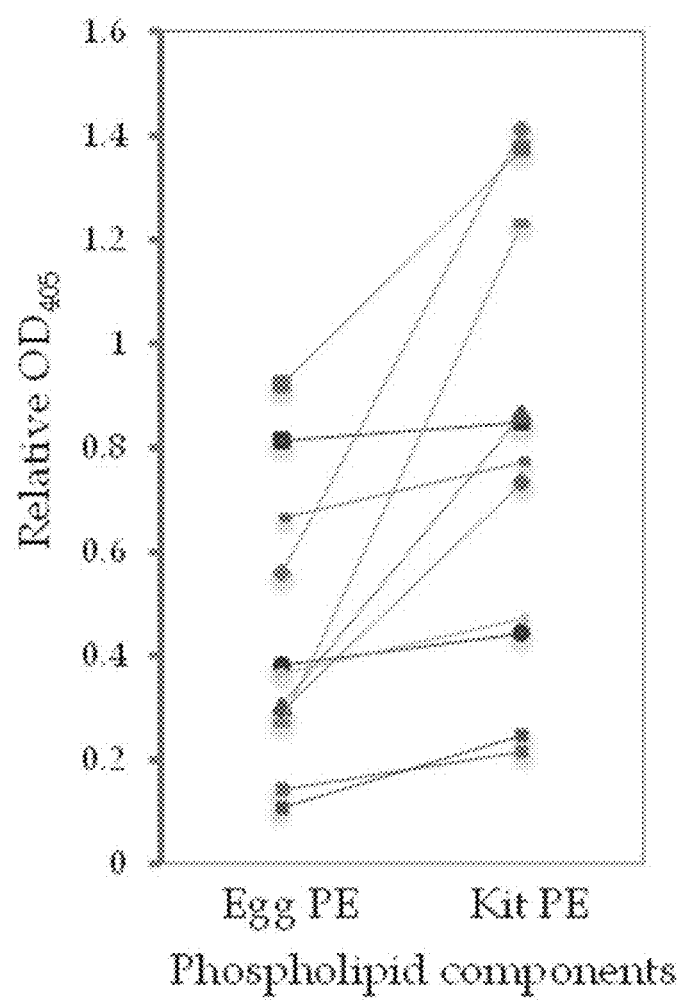

FIG. 13. A head-to-head comparison on the ELISA performance between egg PE and the synthetic formulation. The ELISA place was coated with 0.5 μg of egg PE or the kit formulation (20% 18:0 PE, 13.3% 18:1 PE, 39.9% 20:4 PE, and 26.6% 22:6 PE). OD405 was measured after ELISA and the relative OD value was subtracted from the normal human serum value. The net value was the mean of triplicates. A total 11 patient serum samples were tested for experiments. T test P=0.006, n=11.

Figure 14:
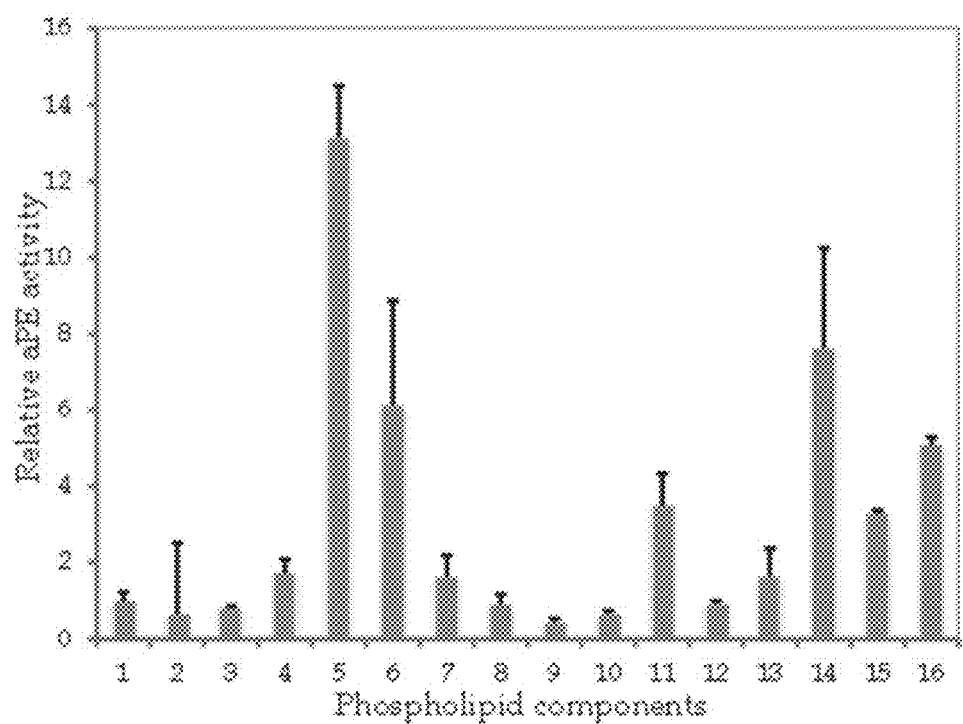

FIG. 14. Screening for optimized synthetic PE formulations for detecting cofactor-independent aPE IgG reactivity and the marked line chart to show 20:4 PE effect on aPE activity. A. 1, Egg PE; 2, 16:0 PE; 3, 18:0 PE; 4, 18:1 PE; 5, 20:4 PE; 6, 22:6 PE; 7, 20% 16:0 PE and 80% 18:1PE; 8, 20% 16:0 PE and 80% 20:4 PE; 9, 20% 16:0 PE and 80% 22:6 PE; 10, 20% 18:0 PE and 80% 18:1PE; 11, 20% 18:0 PE and 80% 20:4 PE; 12, 20% 18:0 PE and 80% 22:6 PE; 13, 10% 16:0 PE, 10% 18:0 PE, 13.3% 18:1 PE, 26.6% 20:4 PE and 39.9% 22:6 PE; 14, 10% 16:0 PE, 10% 18:0 PE, 13.3% 18:1 PE, 39.9% 20:4 PE and 26.6% 22: PE; 15, 20% 16:0 PE, 10% 18:0 PE, 13.3% 18:1 PE, 26.6% 20:4 PE and 39.9% 22:6 PE; 16, 20% 18:0 PE, 13.3% 18:1 PE, 39.9% 20:4 PE and 26.6% 22:6 PE. 1 mg indicated PE was coated on each well of 96 plate, $OD_{405}$ was measured after Elisa and the relative OD value was deducted the normal human serum value and normalized with egg PE value. The error bar represents SEM, n=3. serum was from 1 representative patient sample.

Figure 15:
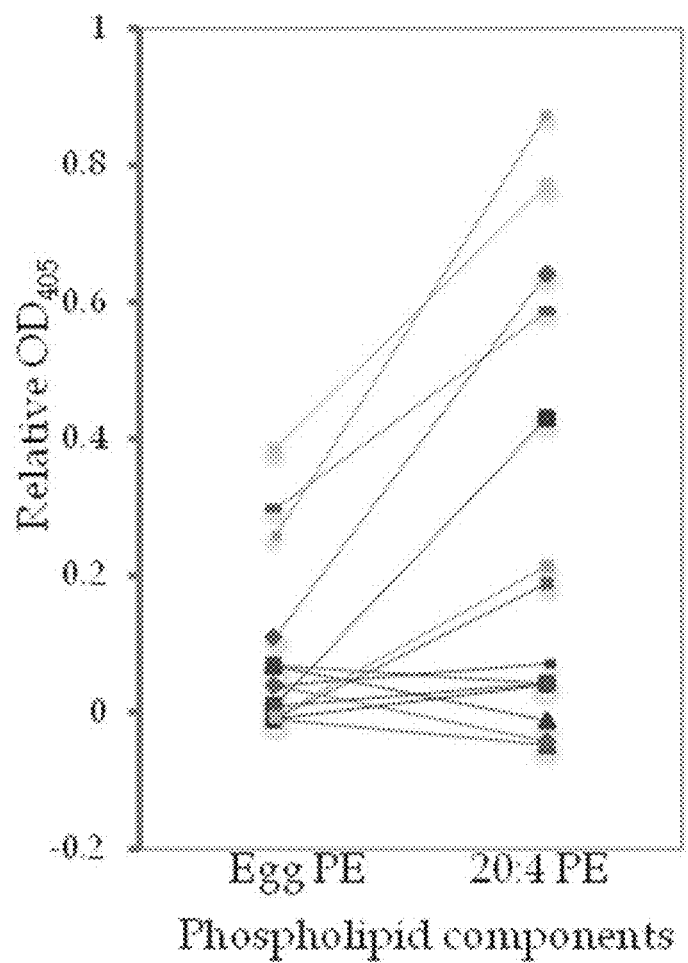

FIG. 15. Head-to-head comparison between egg PE and synthetic 20:4 PE on the ELISA for cofactor-independent aPE IgG reactivity. The 96 well plate was coated with 1 mg of indicated PE per well, $OD_{405}$ was measured after ELISA and the relative OD value was determined by subtracting the OD value of normal human serum from the patient sample. The value is the mean of triplicates. A total 14 patient serums were tested. T test P=0.012, n=14.

Figure 16A:
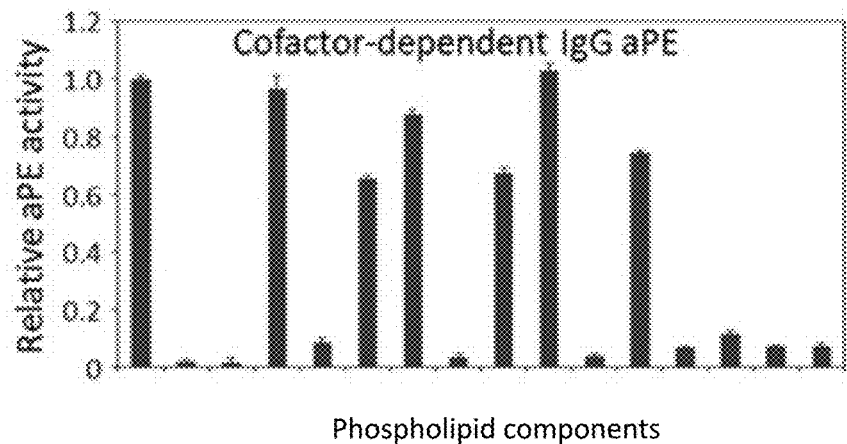
Figure 16B:
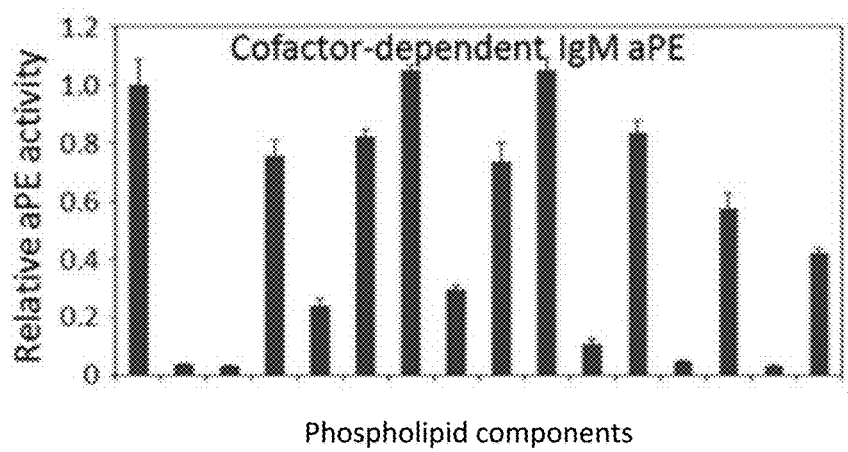
Figure 16C:
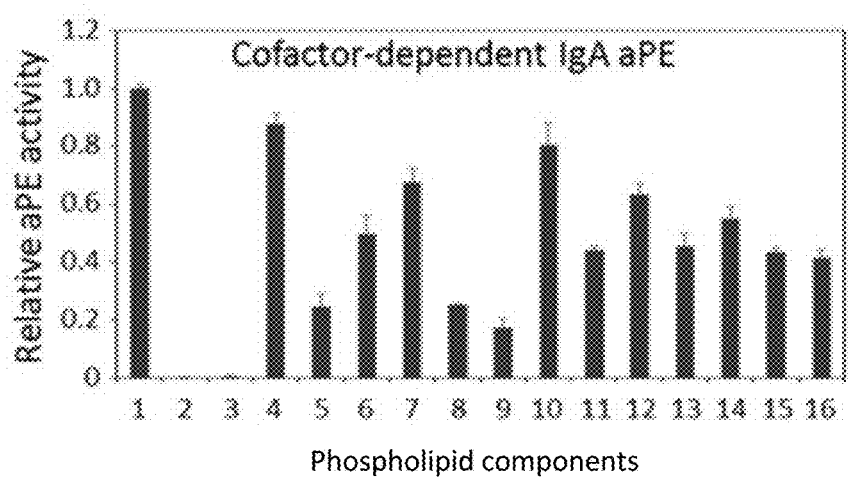

FIGS. 16A-C. Screening phospholipid combinations to detect ABP dependent aPE using representative IgG, IgM and IgA aPE patient plasma samples. 1, Egg PE; 2, 16:0 PE; 3, 18:0 PE; 4, 18:1 PE; 5, 20:4 PE; 6, 22:6 PE; 7, 20% 16:0 PE and 80% 18:1PE; 8, 20% 16:0 PE and 80% 20:4 PE; 9, 20% 16:0 PE and 80% 22:6 PE; 10, 20% 18:0 PE and 80% 18:1PE; 11, 20% 18:0 PE and 80% 20:4 PE; 12, 20% 18:0 PE and 80% 22:6 PE; 13, 10% 16:0 PE, 10% 18:0 PE, 13.3% 18:1 PE, 26.6% 20:4 PE and 39.9% 20:6 PE; 14, 10% 16:0 PE, 10% 18:0 PE, 13.3% 18:1 PE and 39.9% 20:4 PE and 26.6% 20:4 PE; 15, 20% 16:0% 18:0 PE, 13.3% 18:1 PE, 26.6% 20:4 PE and 39.9% 22:6 PE; 16, 20% 18:0 PE, 13.3% 18:1 PE, 39.9% 20:4 PE and 26.6% 22:6 PE. 1 mg indicated PE was coated on each well of 96 plate, $OD_{405}$ was measured after Elisa and the relative OD value was deducted the normal human serum value and normalized with egg PE value. The error bar represents SEM, n=3 in A. the column represents the average of duplicates in B. Serums were from patient E050502W in A and R062303L in B. C. the marked line chart to show 20:4 PE effect on aPE activity. The relative PE was coated on each well of 96 plate, $OD_{405}$ was measured after Elisa and the relative OD value was deducted the normal human serum value. The value is the mean of triplicates. Total 12 patient serums were used for experiments, 8 were IgG aPE serums, 3 were IgM aPE serums and one was IgA aPE serum. T test P=0.9989, n=12.

Figure 17:
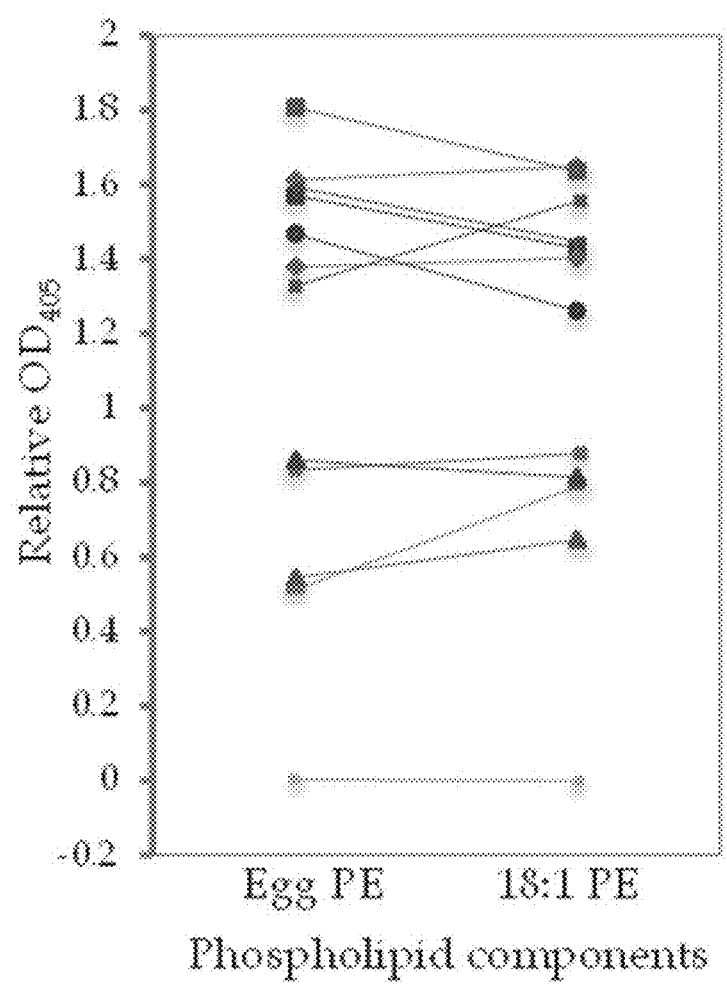

FIG. 17. A head-to-head comparison between 18:1 PE and egg PE on the ELISA detection of cofactor-dependent aPE samples. The PE was coated on each well of 96 plate, $OD_{405}$ was measured after Elisa and the relative OD value was deducted the normal human serum value. The value is the mean of triplicates. Total 12 patient serums were used for experiments, 8 were IgG aPE serums, 3 were IgM aPE serums and one was IgA aPE serum. T test P=0.9989, n=12.

Figure 18:
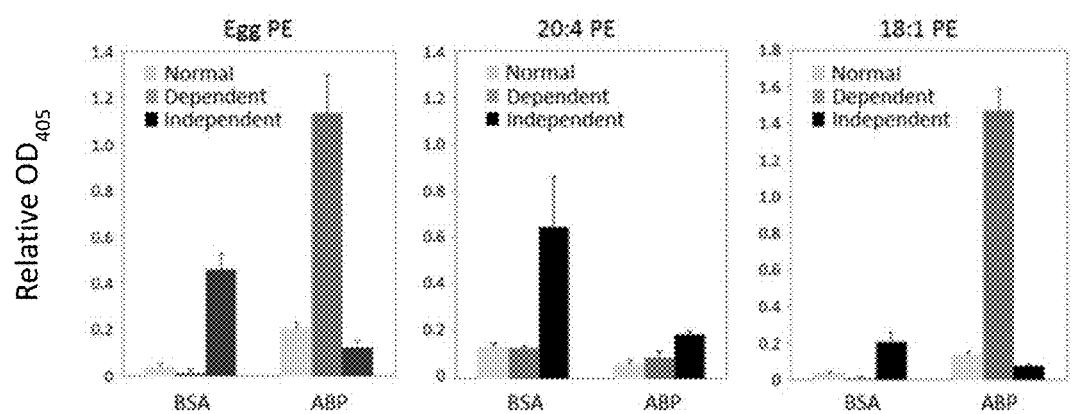

FIG. 18. aPE reactivity to egg PE, 20:4 PE and 18:1 PE using affinity-purified total IgG from a cofactor-dependent and a cofactor-independent IgG aPE patient plasma. For each ELISA test, the total IgG was used at a concentration of 200 μg/ml. The data demonstrated that the cofactor-dependent and cofactor-independent IgG aPE prefer 18:1 PE and 20:4 PE, respectively. The values are means of triplicates.

Figure 19:
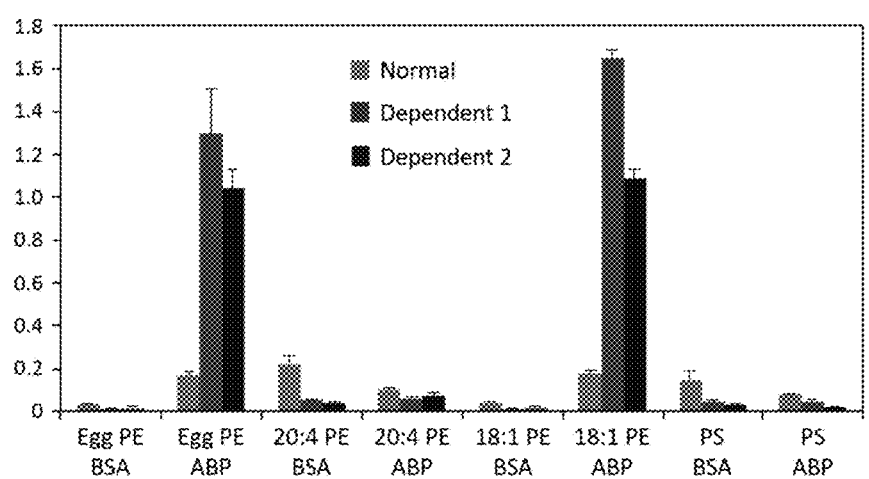

FIG. 19. aPE activity to synthetic PE antigens using affinity purified total IgG from two different patients with cofactor-dependent IgG aPE. The data demonstrated a preference to 18:1 PE as an antigen. The values are means of triplicates.

DEFINITIONS

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a PE species" is a reference to one or more PE species and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

The term "about" allows for a degree of variability in a value or range. As used herein, the term "about: refers to values within 10% of the recited value or range (e.g., about 50 is the equivalent of 45-55).

As used herein, the terms "lipid species," "phospholipid species," and "phosphatidylethanolamine species" refer to a chemically-distinct lipid, phospholipid, or phosphatidylethanolamine molecules. For example, phospholipids of the same species have the same head group and fatty acid chains. Phospholipids with the same head group, but fatty acid chains of different lengths and/or degrees of saturation, are different phospholipid species. PE molecules of the same species have the same head group and fatty acid chains of the same length and saturation characteristics (e.g., 20:4, 18:1, 18:0, etc.).

As used herein, the term "fatty acid" refers to a carboxylic acid with a long aliphatic chain, which is either saturated or unsaturated. Examples of fatty acids that find use in embodiments herein, include:

saturated fatty acid PE species"), both be unsaturated ("mixed unsaturated fatty acid PE species"), or a combination of saturated and unsaturated ("mixed saturated/unsaturated fatty acid PE species").

As used herein, a "saturated PE species" refers to a phospholipid having a phosphatidylethanolamine head group and two saturated fatty acids (typically two of the same fatty acids). As used herein, a "unsaturated PE species" refers to a phospholipid having a phosphatidylethanolamine head group and two unsaturated fatty acids (typically two of the same fatty acids).

As used herein, the term "synthetic" refers to a molecule that is produced through chemical synthesis, rather than being purified from a natural source. A synthetic molecule (e.g., PE) may be synthesized from components (e.g., fatty acids) that are obtained from natural sources.

As used herein, the term "sample" is used herein in its broadest sense. It is meant to include: a specimen, culture, lysate, etc. It includes a prepared solution or mixture, and both biological and environmental collections. Biological samples may take the form of a fluid or solid, may be obtained from any suitable biological source (e.g., animal, including human, microbiological, etc.), and may include blood (e.g., whole blood, leukocytes, peripheral blood mononuclear cells, buffy coat, plasma, and serum), sputum, tears, mucus, nasal washes, nasal aspirate, breath, urine, semen, saliva, peritoneal washings, ascites, cystic fluid, meningeal fluid, amniotic fluid, glandular fluid, lymph fluid, nipple aspirate, bronchial aspirate, bronchial brushing, synovial fluid, joint aspirate, organ secretions, cells, a cellular extract, and cerebrospinal fluid. Environmental samples include environmental material such as surface matter, soil, plants, and water. These examples are not to be construed as

| Common name | Chemical structure | C:D |
| --- | --- | --- |
| Myristoleic acid | $CH_3(CH_2)_3CH=CH(CH_2)_7COOH$ | 14:1 |
| Palmitoleic acid | $CH_3(CH_2)_5CH=CH(CH_2)_7COOH$ | 16:1 |
| Sapienic acid | $CH_3(CH_2)_8CH=CH(CH_2)_4COOH$ | 16:1 |
| Oleic acid | $CH_3(CH_2)_7CH=CH(CH_2)_7COOH$ | 18:1 |
| Elaidic acid | $CH_3(CH_2)_7CH=CH(CH_2)_7COOH$ | 18:1 |
| Vaccenic acid | $CH_3(CH_2)_5CH=CH(CH_2)_9COOH$ | 18:1 |
| Linoleic acid | $CH_3(CH_2)_4CH=CHCH_2CH=CH(CH_2)_7COOH$ | 18:2 |
| Linoelaidic acid | $CH_3(CH_2)_4CH=CHCH_2CH=CH(CH_2)_7COOH$ | 18:2 |
| α-Linolenic acid | $CH_3CH_2CH=CHCH_2CH=CHCH_2CH=CH(CH_2)_7COOH$ | 18:3 |
| Arachidonic acid | $CH_3(CH_2)_4CH=CHCH_2CH=CHCH_2CH=CHCH_2CH=CH(CH_2)_3COO^{NIST}$ | 20:4 |
| Eicosapentaenoic acid | $CH_3CH_2CH=CHCH_2CH=CHCH_2CH=CHCH_2CH=CHCH_2CH=CH(CH_2)_3COOH$ | 20:5 |
| Erucic acid | $CH_3(CH_2)_7CH=CH(CH_2)_{11}COOH$ | 22:1 |
| Docosahexaenoic acid | $CH_3CH_2CH=CHCH_2CH=CHCH_2CH=CHCH_2CH=CHCH_2CH=CHCH_2CH=CH(CH_2)_2COOH$ | 22:6 |
| Caprylic acid | $CH_3(CH_2)_6COOH$ | 8:0 |
| Capric acid | $CH_3(CH_2)_8COOH$ | 10:0 |
| Lauric acid | $CH_3(CH_2)_{10}COOH$ | 12:0 |
| Myristic acid | $CH_3(CH_2)_{12}COOH$ | 14:0 |
| Palmitic acid | $CH_3(CH_2)_{14}COOH$ | 16:0 |
| Stearic acid | $CH_3(CH_2)_{16}COOH$ | 18:0 |
| Arachidic acid | $CH_3(CH_2)_{18}COOH$ | 20:0 |
| Behenic acid | $CH_3(CH_2)_{20}COOH$ | 22:0 |
| Lignoceric acid | $CH_3(CH_2)_{22}COOH$ | 24:0 |
| Cerotic acid | $CH_3(CH_2)_{24}COOH$ | 26:0 |

Unless noted otherwise, phospholipids (e.g., PE species) herein display two of the same fatty acids (e.g., same length and saturation/unsaturation state). For example, as used herein, "18:0 PE" comprises a phosphatidylethanolamine head group and two stearic acid fatty acids. Similarly, "arachidonic PE" or (20:4 PE) comprises a phosphatidylethanolamine head group and two arachidonic acid fatty acids. A PE species displaying two different fatty acids is referred to herein as a "mixed fatty acid PE." In a mixed fatty acid, the two fatty acids may both be saturated ("mixed limiting the sample types applicable to the present invention. Samples also include processed or otherwise separated fractions of all of the preceding. For example, a blood sample can be fractionated into serum, plasma, or into fractions containing particular types of blood cells, such as red blood cells or white blood cells (leukocytes). In some embodiments, a sample can be a combination of samples from an individual, such as a combination of a tissue and fluid sample. The term "sample" may also include materials containing homogenized solid material, such as from a stool sample, a tissue sample, or a tissue biopsy; and materials derived from a tissue culture or a cell culture. A sample may be processed in any suitable manner (e.g., filtered, diluted, pooled, fractionated, concentrated, etc.) after being obtained/provided.

As used herein, the term "analyte" refers to a molecular constituent of a sample (e.g., biological sample, environmental sample, etc.) that can be detected, quantified, and/or analyzed by appropriate methods (e.g., immunoassay). Analytes may be naturally occurring substances (e.g., obtained/provided from a biological or environmental sample) or artificial substances (e.g., synthesized). Exemplary analytes is embodiments herein are antibodies (aPE antibodies).

As used herein, the term "antibody" refers to a whole antibody molecule or a fragment thereof (e.g., fragments such as Fab, Fab', and F(ab')$_2$), unless specified otherwise. Embodiments referring to "an antibody" encompass multiple embodiments including "a whole antibody" and fragments of the antibody, which may alternatively be claimed or described using such language.

A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, $V_H$, and three constant regions, $C_{H1}$, $C_{H2}$, and $C_{H3}$. The $V_H$ domain is at the amino-terminus of the heavy chain, and the $C_{H3}$ domain is at the carboxy-terminus. In a native antibody, a light chain comprises a variable region, $V_L$, and a constant region, $C_L$. The variable region of the light chain is at the amino-terminus of the light chain. In a native antibody, the variable regions of each light/heavy chain pair typically form the antigen binding site. The constant regions are typically responsible for effector function.

In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen-binding site. H3, for example, in certain instances, can be as short as two amino acid residues or greater than 26. The assignment of amino acids to each domain is typically in accordance with the definitions of Kabat et al. (1991) Sequences of Proteins of Immunological Interest (National Institutes of Health, Publication No. 91-3242, vols. 1-3, Bethesda, Md.); Chothia, C., and Lesk, A. M. (1987) J. Mol. Biol. 196:901-917; or Chothia, C. et al. Nature 342:878-883 (1989). In the present application, the term "CDR" refers to a CDR from either the light or heavy chain, unless otherwise specified.

Native human light chains are typically classified as kappa and lambda light chains. Native human heavy chains are typically classified as mu, delta, gamma, alpha, or epsilon, and define the antibody's isotype as IgM, IgD, IgG, IgA, and IgE, respectively. IgG has subclasses, including, but not limited to, IgG1, IgG2, IgG3, and IgG4. IgM has subclasses including, but not limited to, IgM1 and IgM2. IgA has subclasses including, but not limited to, IgA1 and IgA2. Within native human light and heavy chains, the variable and constant regions are typically joined by a "J" region of about 12 or more amino acids, with the heavy chain also including a "D" region of about 10 more amino acids. See, e.g., Fundamental Immunology (1989) Ch. 7 (Paul, W., ed., 2nd ed. Raven Press, N.Y.); herein incorporated by reference in its entirety.

As used herein, when an antibody or other entity "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant ($K_a$) of at least $10^7$ $M^{-1}$ (e.g., $>10^7 M^{-1}$, $>10^8 M^{-1}$, $>10^9 M^{-1}$, $>10^{10} M^{-1}$, $>10^{11} M^{-1}$, $>10^{12} M^{-1}$, $>10^{13} M^{-1}$, etc.). In certain such embodiments, an antibody is capable of binding different antigens so long as the different antigens comprise that particular epitope. In certain instances, for example, homologous proteins from different species may comprise the same epitope.

As used herein, the term "antibody fragment" refers to a portion of a full-length antibody, including at least a portion antigen binding region or a variable region. Antibody fragments include, but are not limited to, Fab, Fab', F(ab')$_2$, Fc, Fv, scFv, Fd, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody) produced by recombinant DNA techniques, or chemical polypeptide synthesis.

DETAILED DESCRIPTION

Provided herein are compositions comprising distinct lipid species in defined ratios and methods of use thereof for the detection of anti-phosphatidylethanolamine (aPE) antibodies and diagnosis of antiphospholipid syndrome (APS).

Accumulating evidence supports a positive correlation between the presence of antiphosphatidylethanolamine (aPE) autoantibodies and clinical symptoms of antiphospholipid syndromes (APS). However, there lacks a standardized method (e.g., ELISA-based method) for detecting aPE. Experiments were conducted during development of herein to determine the dependence of aPE ELISA on lipid concentration and composition of PE antigens. Data indicated that there are different optimal PE concentrations for conducting ELISA assays for cofactor dependent and independent aPE. In addition, using a two-component synthetic lipid system, experiments conducted during development of embodiments herein demonstrated that aPE ELISA readouts can be modulated to approach the performance level of egg PE, which is currently the most commonly used PE antigen. These data indicate replacing natural PE antigens with a blend of defined synthetic lipid species, thus overcoming a known variable factor in aPE detection.

Currently, aPE ELISA assays involve variable reagents and protocols among laboratories, which contribute to inconsistent comparisons of aPE ELISA data. The source of antigen PE has been considered as one of the parameters that affect the sensitivity and reproducibility of ELISA (ref. 14; herein incorporated by reference in its entirety). Egg yolk is currently the most common source of antigen PE used in aPE ELISA. PE compositions from nature sources, such as the egg, brain or bacteria, can be highly variable, differing in fatty acid compositions, such as the length of the fatty acid chains, as well as the ratios and locations of saturated to unsaturated bonds in acyl chains. The differences between manufacturers or even different batches from one manufacturer affect the packing and conformation of lipid molecules, contributing to uncertainties in aPE detection. To this end, synthetic lipids are chemically homogenous. In some embodiments, provided herein is a blend of synthetic lipids with defined composition that mimic the antigenic properties of natural PE.

In some embodiments, provided herein are compositions comprising one or more PE species. In some embodiments, a composition comprises only a single PE species. In some embodiments, a composition comprises multiple (e.g., 2, 3, 4, 5, 6, 7, 8, 9 10, or more, or ranges therebetween (e.g., 2-6)) PE species. In some embodiments, a PE species comprises two fatty acid chains of identical length and saturation. In some embodiments, a PE species with two fatty acid chains of identical length and saturation is referred to by C:D number (e.g., 16:0, 18:0, 18:1, 20:4, 22:6, etc.) or common name (e.g., Eicosapentaenoic PE, Palmitoleic PE, etc.). In some embodiments, a PE species comprises two fatty acid chains of different lengths and/or saturation. In some embodiments, a PE species with two fatty acid chains of identical length and saturation is referred to by common names of the fatty acids (e.g., docosahexaenoic/oleic PE, etc.). In some embodiments, suitable PE species for use in the compositions, kits, and methods described herein include, but are not limited to: 8:0 PE, 12:0 PE, 14:0 PE, 14:1 PE, 16:0 PE, 16:1 PE, 18:0 PE, 18:1 PE, 18:2 PE, 18:3 PE, 20:0 PE, 20:4 PE, 20:5 PE, 22:0 PE, 22:1 PE, 22:6 PE, 24:0 PE, etc. In some embodiments, suitable PE species for use in the compositions, kits, and methods described herein include, but are not limited to: myristoleic PE, palmitoleic PE, sapienic PE, oleic PE, elaidic PE, vaccenic PE, linoleic PE, linoelaidic PE, α-linolenic PE, arachidonic PE, eicosapentaenoic PE, erucic PE, docosahexaenoic PE, caprylic PE, capric PE, lauric PE, myristic PE, palmitic PE, stearic PE, arachidic PE, behenic PE, lignoceric PE, cerotic PE, etc.

In some embodiments, a composition comprises at least one saturated and one unsaturated PE. In some embodiments, the composition comprises a defined ratio of saturated to unsaturated PE. In some embodiments, compositions comprise 1-40% (e.g., 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, or ranges therebetween (e.g., 5-30%, 10-25%, 15-22%, etc.)) saturated PE and 60-99% (e.g., 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or ranges therebetween (e.g., 70-95%, 75-90%, 78-85%, etc.)) unsaturated PE. In some embodiments, multiple (e.g., 2, 3, 4, 5, 6, 7, 8, 9, 10, 20, 50, 100, 200, 500, 1000, or more) separately contained compositions comprise the same defined ratio of saturated to unsaturated PE. In some embodiments, the saturated PE is 8:0, 10:0, 12:0, 14:0, 16:0, 18:0, 20:0, 22:0, and/or 24:0. In some embodiments, the saturated PE is 16:0 and/or 18:0. In some embodiments, the unsaturated PE is 16:1 PE, 18:1 PE, 18:2 PE, 18:3 PE, 20:4 PE, 20:5 PE, 22:1 PE, and/or 22:6 PE. In some embodiments, the unsaturated PE is 18:1, 20:4 and/or 22:6.

In some embodiments, a composition comprises 2 distinct PE species. In some embodiments, a composition comprises 3 distinct PE species. In some embodiments, a composition comprises 4 distinct PE species. In some embodiments, a composition comprises 5 distinct PE species. In some embodiments, a composition comprises 6 distinct PE species. In some embodiments, a composition comprises 7 distinct PE species.

In some embodiments, a composition comprises 5-40% (e.g., 10-30%, 15-25%, 16-24%, 17-23%, 18-22%, 19-21%, 20%) saturated PE (e.g., 8:0, 10:0, 12:0, 14:0, 16:0, 18:0, 20:0, 22:0, and/or 24:0) and 60-95% (e.g., 70-90%, 75-85%, 76-84%, 77-83%, 78-82%, 79-81%, 80%) unsaturated PE (e.g., 16:1 PE, 18:1 PE, 18:2 PE, 18:3 PE, 20:4 PE, 20:5 PE, 22:1 PE, and/or 22:6 PE). In some embodiments, the 5-40% (e.g., 10-30%, 15-25%, 16-24%, 17-23%, 18-22%, 19-21%, 20%) saturated PE comprises 2 saturated PE species (e.g., 16:0 and 18:0). In some embodiments, the 5-40% (e.g., 10-30%, 15-25%, 16-24%, 17-23%, 18-22%, 19-21%, 20%) saturated PE comprises a single saturated PE species (e.g., 16:0 or 18:0). In some embodiments, the 60-95% (e.g., 70-90%, 75-85%, 76-84%, 77-83%, 78-82%, 79-81%, 80%) unsaturated PE comprises a single species (e.g., 16:1 PE, 18:1 PE, 18:2 PE, 18:3 PE, 20:4 PE, 20:5 PE, 22:1 PE, or 22:6 PE). In some embodiments, the 60-95% (e.g., 70-90%, 75-85%, 76-84%, 77-83%, 78-82%, 79-81%, 80%) unsaturated PE comprises a 2 species (e.g., 16:1 PE, 18:1 PE, 18:2 PE, 18:3 PE, 20:4 PE, 20:5 PE, 22:1 PE, and/or 22:6 PE). In some embodiments, the 60-95% (e.g., 70-90%, 75-85%, 76-84%, 77-83%, 78-82%, 79-81%, 80%) unsaturated PE comprises a 3 species (e.g., 16:1 PE, 18:1 PE, 18:2 PE, 18:3 PE, 20:4 PE, 20:5 PE, 22:1 PE, and/or 22:6 PE). In some embodiments, the 60-95% (e.g., 70-90%, 75-85%, 76-84%, 77-83%, 78-82%, 79-81%, 80%) unsaturated PE comprises a 4 species (e.g., 16:1 PE, 18:1 PE, 18:2 PE, 18:3 PE, 20:4 PE, 20:5 PE, 22:1 PE, and/or 22:6 PE). In some embodiments, the 60-95% (e.g., 70-90%, 75-85%, 76-84%, 77-83%, 78-82%, 79-81%, 80%) unsaturated PE comprises a 5 species (e.g., 16:1 PE, 18:1 PE, 18:2 PE, 18:3 PE, 20:4 PE, 20:5 PE, 22:1 PE, and/or 22:6 PE). In some embodiments, the 60-95% (e.g., 70-90%, 75-85%, 76-84%, 77-83%, 78-82%, 79-81%, 80%) unsaturated PE comprises a 6 species (e.g., 16:1 PE, 18:1 PE, 18:2 PE, 18:3 PE, 20:4 PE, 20:5 PE, 22:1 PE, and/or 22:6 PE). In some embodiments, each of the unsaturated PE species in a composition is present in 5-95% (e.g., 5%, 10%, 15%, 20%, 25%, 30%, 35%, 40%, 45%, 50%, 55%, 60%, 65%, 70%, 75%, 80%, 85%, 90%, 95%, or ranges therebetween).

In some embodiments, a composition comprises 10-30% (e.g., 10%, 12%, 14%, 16%, 18%, 20%, 22%, 24%, 26%, 28%, 30%, or ranges therebetween) 16:0 PE and/or 18:0, and 10-50% (e.g., %, 10%, 15%, 20%, 25%, 30%, 35%, 40%, 45%, 50%, or ranges therebetween) of each of 2-4 of 16:1 PE, 18:1 PE, 18:2 PE, 18:3 PE, 20:4 PE, 20:5 PE, 22:1 PE, and/or 22:6 PE. In some embodiments, a composition comprises 10-30% (e.g., 10%, 12%, 14%, 16%, 18%, 20%, 22%, 24%, 26%, 28%, 30%, or ranges therebetween) 16:0 PE and/or 18:0, and 10-50% (e.g., %, 10%, 15%, 20%, 25%, 30%, 35%, 40%, 45%, 50%, or ranges therebetween) of each of 18:1 PE, 20:4 PE, and 22:6 PE. In some embodiments, a composition comprises 10-30% (e.g., 10%, 12%, 14%, 16%, 18%, 20%, 22%, 24%, 26%, 28%, 30%, or ranges therebetween) 16:0 PE and/or 18:0, and 10-50% (e.g., %, 10%, 15%, 20%, 25%, 30%, 35%, 40%, 45%, 50%, or ranges therebetween) of each of 18:1 PE, 20:4 PE, and 22:6 PE. In some embodiments, a composition comprises 15-25% (e.g., 15%, 16%, 17%, 18%, 19%, 20%, 21%, 22%, 23%, 24%, 25%, or ranges therebetween) 16:0 PE and/or 18:0, and 6-20% (e.g., 6%, 8%, 10%, 12%, 14%, 16%, 18%, 20%, or ranges therebetween) 18:1 PE, 20-60% (e.g., 20%, 25%, 30%, 35%, 40%, 45%, 50%, 55%, 60%, or ranges therebetween) 20:4 PE, and 10-40% (e.g., 10%, 15%, 20%, 25%, 30%, 35%, 40%, or ranges therebetween) 22:6 PE. In some embodiments, a composition comprises about 20% 18:0 PE, about 13.3% 18:1 PE, about 39.9% 20:4 PE, and about 26.6% 22:6 PE.

In some embodiments, a composition is provided with a definite formulation of PE species. In some embodiments, the compositions exhibits enhanced ELISA performance (e.g., increased relative aPE activity) when compared to a PE reagent obtained from egg or other natural source. In some embodiments, the concentration of each PE species in a composition is known. In some embodiments, the relative concentrations (e.g., as a ratio) of each PE species in a composition is known.

In some embodiments, the concentration of a PE species in a composition (e.g., ELISA reagent) is between 0.1 µg/ml and 1000 µg/ml (e.g., 0.1 µg/ml, 0.2 µg/ml, 0.5 µg/ml, 1 µg/ml, 2 µg/ml, 5 µg/ml, 10 µg/ml, 20 µg/ml, 50 µg/ml, 500 µg/ml, 1000 µg/ml, and ranges therebetween).

In some embodiments, provided herein are containers (e.g., well, tube, etc.) and/or devices (e.g., 96-well plate, 384-well plate, etc.) comprising the PE-containing compositions described herein. In some embodiments, a liquid composition comprising a defined formulation of PE species is applied to a container or device (e.g., one or more wells of a microwell plate), and the composition is dried (e.g., under vacuum, under heat, etc.) to dry the PE composition onto a surface of the container or device (e.g., sidewall, bottom, etc.). In some embodiments, provided herein are microwell plates (e.g., 96-well plate, 384-well plate), conical tubes, etc. comprising a defined-formulation PE-containing reagent described herein loaded within one or more wells, and or dried to the bottom and/or sidewalls of one or more wells.

In some embodiments, any suitable amount of defined-formulation PE-containing reagent may be used in a device and/or in an assay described herein. In some embodiments, an amount of defined-formulation PE-containing reagent corresponding to 0.1 to 2 µg (e.g., 0.1 µg, 0.2 µg, 0.3 µg, 0.4 µg, 0.5 µg, 0.6 µg, 0.7 µg, 0.8 µg, 0.9 µg, 1.0 µg, 1.1 µg, 1.2 µg, 1.3 µg, 1.4 µg, 1.5 µg, 1.6 µg, 1.7 µg, 1.8 µg, 1.9 µg, 2.0 µg, or ranges therebetween (e.g., 0.25 to 0.5 µg)) per well in a 96 well ELISA plate is coated/dried onto a surface and/or device.

In some embodiments, provided herein are reaction mixtures comprising defined-formulation PE-containing compositions and aPE antibodies. In some embodiments, provided herein are reaction mixtures comprising synthetic defined-formulation PE-containing compositions and natural-source aPE antibodies.

Embodiments herein find use in the detection and/or quantification of aPE antibodies in a sample (e.g., from a subject). Assays, devices (e.g., fluorimeter, luminometer, surface, etc.), and reagents are provided for the detection/quantification of aPE antibodies.

In some embodiments, kits and systems are provided for assaying a sample (e.g., blood sample, processed blood product, etc.) for the presence and/or amount (e.g., concentration) of anti-phosphatidylethanolamine (aPE) antibodies. In some embodiments, kits and systems are provided for performing an immunoassay (e.g., ELISA (e.g., competitive ELSIA, sandwich ELISA, etc.). Enzyme linked immunosorbent assays (ELISA), or Ligand Binding Assays (LBA), are used for analyte detection, and in particular antibody detection, in research, diagnostics, therapeutic development, etc. A "sandwich" ELISA provides high sensitivity for detection of antibodies (e.g., aPE antibodies). In a sandwich ELISA, an antigen for the antibody to be detected is immobilized on a surface, a sample containing (or suspected to contain) the antibody of interest (e.g., aPE) is added to the surface, and a labeled secondary antibody (or antibody fragment) capable of binding to the antibody of interest is added. After washing away unbound components, detection of the label reveals the presence and/or quantity of the antibody of interest in the sample. The assay is referred to as a sandwich ELISA because the antibody to be detected is "sandwiched" between the antigen and the labeled secondary antibody. The sensitivity of a sandwich assay is maximized by using high concentrations of immobilized antigen and secondary detection antibody. The signal from the label increases proportionally to the amount or concentration of the antibody (e.g., aPE) in the sample, and reaches a plateau as the surface is saturated. In a competitive ELISA, an antigen for the antibody to be detected is immobilized on a surface, a sample containing (or suspected to contain) the antibody of interest (e.g., aPE) is added to the surface along with a known amount/concentration of labeled reference antibody that is also capable of binding to the antigen. If the antibody is present in the sample, it will compete with the labeled reference antibody for binding to the immobilized antigen. The signal in a competitive ELISA decreases as the concentration of antibody of interest in the sample increases. The defined-formulation PE-containing compositions described herein find use at the antigen in sandwich and/or competitive ELISAs, as well as in other immunoassays, or other applications in which a known concentration of PE is desired.

In some embodiments, the assays described herein are performed on a surface. Any suitable surface to which PE species within a composition described herein may be immobilized will find use in embodiments herein. In some embodiments, a surface is any solid or stationary material to which PE is attached. Examples of surfaces include microscope slides, wells of microtiter plates, coverslips, beads, particles, resin, cell culture flasks, as well as many other suitable items. In some embodiments, a surface is coated and/or functionalized to facilitate the attachment of PE. In some embodiments, a surface displays (e.g., with or without specific functionalization) one or more moieties to facilitate immobilization of a PE to the surface. In some embodiments, following immobilization of the PE (e.g., from the defined formulation PE-containing composition) to the surface, the remaining exposed surface is blocked to prevent non-specific binding. In some embodiments, blocking comprises immobilizing an inert agent to the surface. In some embodiments, blocking comprises neutralizing or inactivating potentially-reactive sites on the surface.

In some embodiments, the assays described herein utilize a secondary antibody. In some embodiments, a secondary antibody binds to aPE antibodies. In some embodiments, a secondary antibody binds to aPE that is bound to PE. In some embodiments, a secondary antibody binds IgG and/or IgM. In some embodiments, a secondary antibody binds IgG aPE. In some embodiments, the secondary antibody is labeled. Any label that facilitates the monitoring of the binding of the secondary antibody to the PE-bound aPE antibody finds use in embodiments herein. In some embodiments, a label is, for example, an enzyme (e.g., akaline phosphatase (AP) and horseradish peroxidase (HRP), etc.), a radioactive label (e.g., radionuclides), a chromophore (e.g., a dye or particle that imparts a detectable color), a luminescent moiety (e.g., bioluminescent (e.g., photoprotein, luciferase (e.g., renilla, firefly, etc.), etc.), phosphorescent or chemiluminescent label), or a fluorescent moiety (e.g., fluorescent protein (e.g. green fluorescent protein (GFP), enhanced GFP (EGFP), yellow fluorescent protein (YFP), cyan fluorescent protein (CFP), etc.), fluorophore (e.g., xanthene derivatives, cyanine derivatives, etc.).

In some embodiments, a wash step and wash reagents are employed between the steps in the assays described herein (e.g., after immobilization of the PE to a surface, after binding of aPE from the sample to the immobilized antigen, etc.). In some embodiments, the wash step removes unbound components. In some embodiments, wash reagents comprise water, buffer(s), salts, detergents, surfactants, etc. In some embodiments, a wash reagents comprise any components that facilitate the removal of unwanted contaminants (e.g., components of the assay that have already been used and/or are not necessary/desired for subsequent assay steps) without disrupting the assay components (e.g., without de-immobilizing the PE antigen from the surface, without disassociating the aPE antibody from the PE, without disassociating the labeled secondary antibody from the aPE, etc.).

In some embodiments, methods, compositions, kits, and/or systems are provided for the detection of aPE antibodies in a sample. In some embodiments, methods, compositions, kits, and/or systems are configured for detection/quantification of co-factor dependent binding of aPE antibodies to PE (e.g., compositions contain and/or methods are performed in the presence of a reagent comprising co-factor (e.g., androgen binding protein), 18:1 PE is the dominant (e.g., >30%, >40%, >50%, >60%, >70%, >80%, >90%, >95%, >99%) PE species present, etc.). In some embodiments, methods, compositions, kits, and/or systems are configured for detection/quantification of co-factor independent binding of aPE antibodies to PE (e.g., compositions contain and/or methods are performed in the absence of a reagent comprising co-factor (e.g., androgen binding protein), 20:4 PE is the dominant (e.g., >30%) PE species present, etc.). In some embodiments, methods, compositions, kits, and/or systems are configured for (or optimized for) detection/quantification of IgM aPE antibody binding to PE (e.g., 20:4 PE is the dominant species present (e.g., >30%)). In some embodiments, methods, compositions, kits, and/or systems are configured for (or optimized for) detection/quantification of IgA aPE antibody binding to PE (e.g., 20:4 PE is the dominant species present (e.g., >30%)). In some embodiments, methods, compositions, kits, and/or systems are configured for (or optimized for) detection/quantification of IgG aPE antibody binding to PE (e.g., 20:4 PE is the dominant and/or only PE species present (e.g., >30%)).

In some embodiments, in performing the immunoassays described herein reference standards and/or samples comprising known amounts of aPE antibody are used to generate calibration curves and/or signal values that correspond to concentrations of aPE in a sample. In some embodiments, using these calibration curves and/or reference signal values, assay results for samples comprising unknown amounts of aPE are compared the reference to identify the amount of aPE present in the sample.

Certain steps and methods associated with the assays described herein (e.g., data acquisition, data analysis, communication, etc.) are performed by (or cannot be performed without) a computer, processor, software, and/or other device. All or a portion of the methods described herein may be computer-implemented methods, and one or more portions of a method sometimes are performed by one or more processors. In some embodiments, an automated method is embodied in software, processors, peripherals and/or an apparatus comprising the like. As used herein, software refers to computer readable program instructions that, when executed by a processor, perform computer operations, as described herein. In some embodiments, reference values, are stored in a memory element (e.g., comprising a database), and the reference values are accessed by a processor to compare to experimentally acquired data. In some embodiments, calculations are performed by processors, computers, software, etc. to acquire data using the methods described herein (e.g., measure signal from detectable labels), process the data (e.g., plot the data, calculate ratios, regression analysis, calculate derivatives or integrals of data, etc.), compare data to stored reference values (e.g., thresholds, concentrations of analyte, etc.), etc. In some embodiments, instructions, calculations, storage, etc. utilize a non-transitory memory component (e.g., coupled to a processor).

EXPERIMENTAL

Example 1

Materials and Methods

Patients

The study was approved by the Northwestern University Institutional Review Board and was conducted under NIH guidelines. Patient serum samples were provided by the HLA-Vascular Biology Laboratory, Franciscan St. Francis Health, Indianapolis, Ind. Twenty-four aPE-positive serum samples were included for this study. Ten were cofactor-dependent IgG, three were cofactor-independent IgG, three were cofactor dependent IgM, and eight were cofactor-independent IgM. Blood was collected into serum separator vacutainer tubes without anticoagulant and serum was separated by centrifugation. Pooled normal serum control was included in each assay. Aliquots were stored frozen at −70° C. until use.

Phospholipids

All phospholipids were purchased from Avanti Polar Lipids and used without further purification. The concentrations of phospholipid stocks were determined by the Bartlett method (ref. 16; herein incorporated by reference in its entirety).

ELISA

Cofactor-Independent Patients

For aPE ELISA assays (ref. 14; herein incorporated by reference in its entirety), microtiter plates (PolySorp, Thermo Fisher, Pittsburgh, USA) were coated with 50 µl of a solution containing various concentrations of egg yolk PE or equal molar amounts of DOPE in ethanol:chloroform (4:1) and dried by evaporation at room temperature (RT) in an extractor shielded from light. Each well was blocked for two hours at RT with 10% BSA in PBS followed by 50 µl of patient serum diluted 1/100 in PBS for one hour at RT. aPEs were assessed by using alkaline phosphatase conjugated polyclonal antibody (Ab) against either human IgG or IgM. The plates were washed three times with PBS after blocking, serum and conjugate incubations. After color development with paranitrophenyl phosphate as substrate, optical density at 405 nm was measured. OD values of pooled normal serum control were subtracted from those of patient serum samples measured with the same PE concentration. For each patient sample measured with various PE concentrations, OD variations were expressed as the percentage of the highest OD value obtained among various PE concentrations.

Cofactor-Dependent Patients aPE ELISA assays were performed as for plasma protein-dependent patients, with modifications. After being coated with phospholipids, ELISA wells were blocked for two hours at RT with 10% BSA in TBS followed by 50 µl of patient serum diluted 1/100 in TBS in the presence or absence of 10% adult bovine plasma (ABP) for one hour at RT. aPEs were then assessed by using alkaline phosphatase conjugated polyclonal Ab against human IgG.

DSC Measurements

DSC (differential scanning calorimetry) measurements were made using a TA Instruments (New Castle, Del.) Q20 differential scanning calorimeter. Mixed samples were made by adding appropriate amounts of DOPE and DSPE to a sample pan for a total lipid sample of a few mg. High purity cyclohexane (Sigma Aldrich) was added to dissolve and mix the lipids; the cyclohexane was evaporated off and the weight of the sample pan checked to insure all of the solvent had evaporated. An amount of de-ionized water matching or exceeding the lipid weight was added and the sample was sealed using a Tzero hermetic lid and Tzero press (TA Instruments). Samples were heated and cooled at 0.2° C./s to ensure mixing and were then heated and cooled at least twice at rates of 0.1, 0.05, 0.02 and 0.01° C./s. The phase transition temperature seen on heating was plotted versus the temperature seen on cooling and fit to a straight line; the equilibrium transition temperature was found by determining the intersection of this line and the line where the heating and cooling temperatures are equal.

Results

Influence of PE Concentration on aPE Detection

Figure 1:
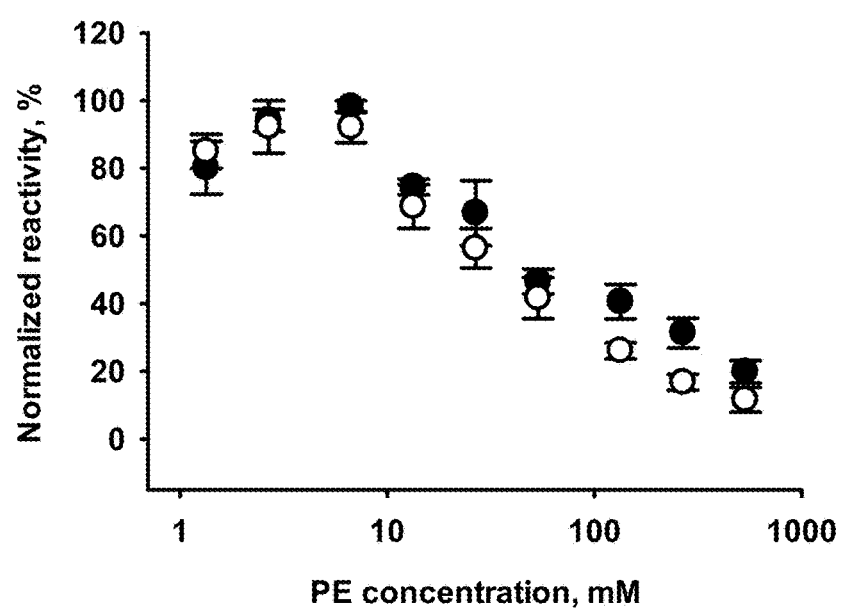
FIG. 1. An example of normalized cofactor-independent aPE reactivities with increasing egg yolk PE (o) or DOPE (•) concentrations. Background aPE reactivities for pooled normal serum were subtracted from aPE reactivities for patient serum obtained at the same PE concentration. Then aPE reactivities for patient serum at certain concentration were normalized to aPE reactivities obtained at the optimum PE concentration. Data are mean±SD, n=3.

In order to determine the optimal concentration of antigen in aPE ELISA, wells were coated with a series of concentrations of egg yolk PE ranging from 1 to 400 µg/ml aPEs or normal control serum were assessed with alkaline phosphatase conjugated polyclonal Ab to either IgG or IgM. For each sample, the OD values of pooled normal serum indicating the level of non-specific binding were systematically subtracted from the OD values obtained with patient serum at the same PE concentration. OD values of each patient serum sample at different PE concentrations, ranging from 1 to 400 µg/ml, were normalized to the highest OD value obtained for the patient. FIG. 1 shows an example of normalized independent aPE reactivities as a function of egg yolk PE or synthetic DOPE concentrations from a representative patient serum. With increasing antigen concentrations from 1 to 400 µg/ml, aPE reactivities increased and peaked at around 5 µg/ml, then gradually decreased.

Figure 2A:
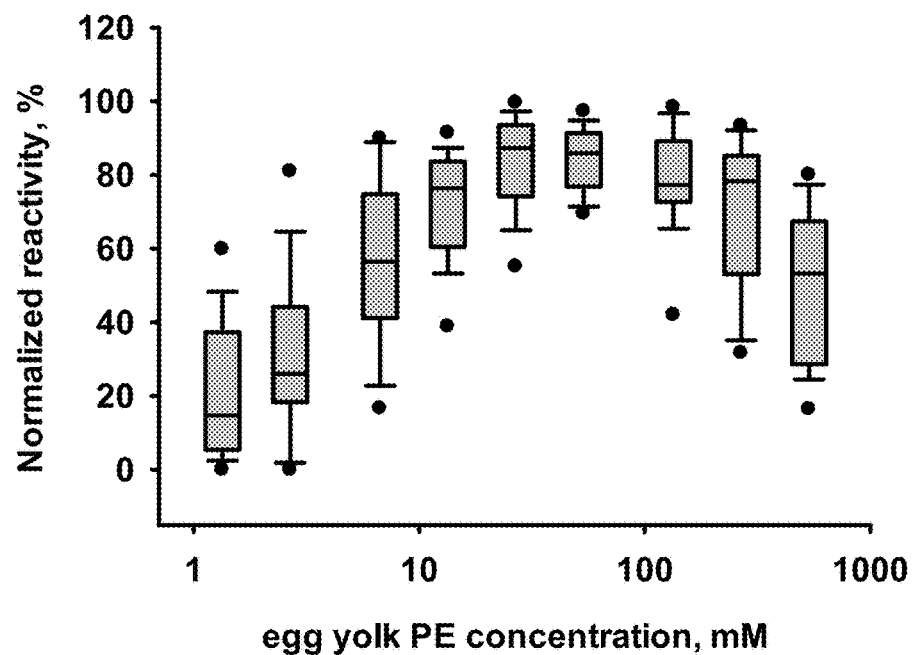
FIGS. 2A-D. Box plot of normalized aPE reactivities with increasing egg yolk PE (A and C) or DOPE (B and D) concentrations. Top panels (A and B) are patients with cofactor-dependent aPE, n=13; bottom panels (C and D) are serum samples with independent aPE, n=11. The box gives the 25th to 75th percentiles, with the median given by the line inside the box. Whiskers above and below the box indicate the 10th and 90th percentiles, with outliers given by dots.
Figure 2B:
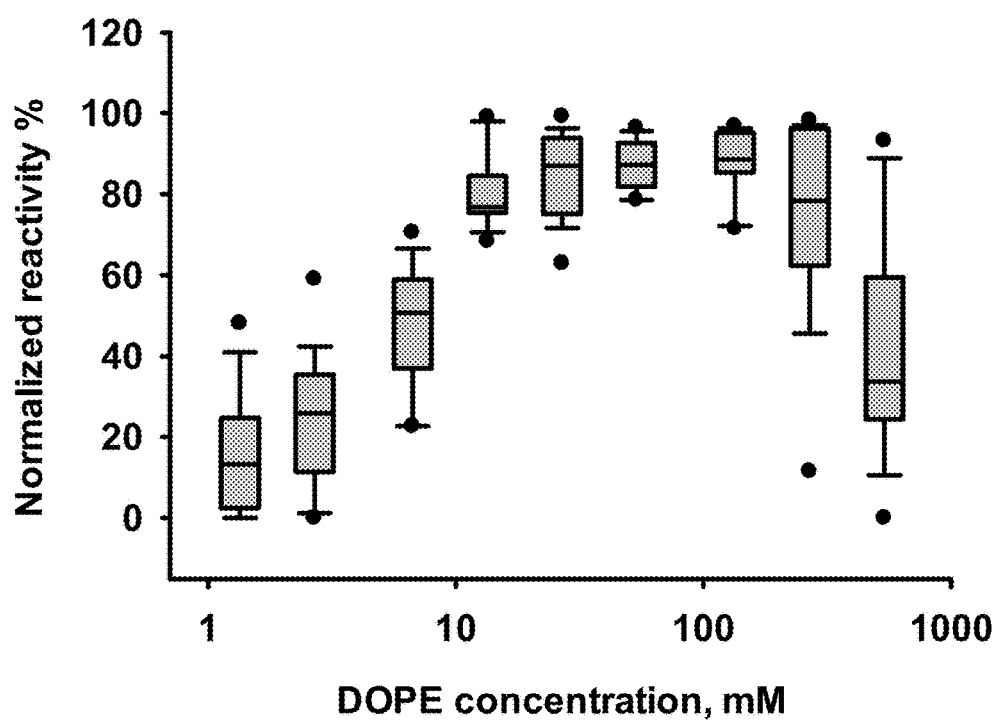
Figure 2C:
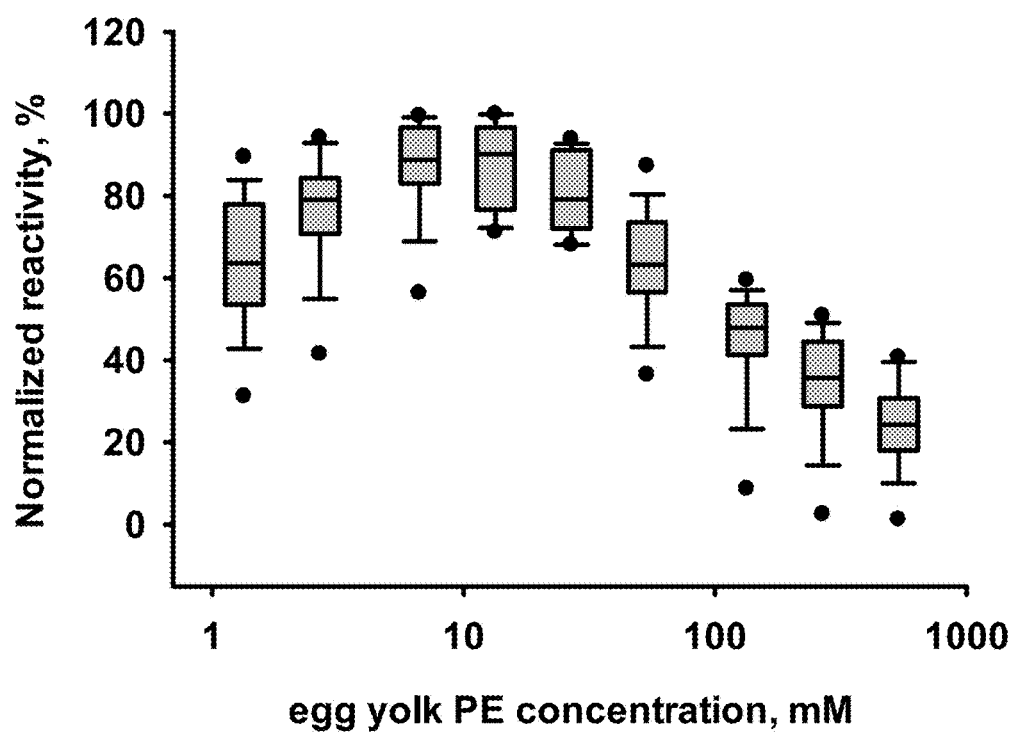
Figure 2D:
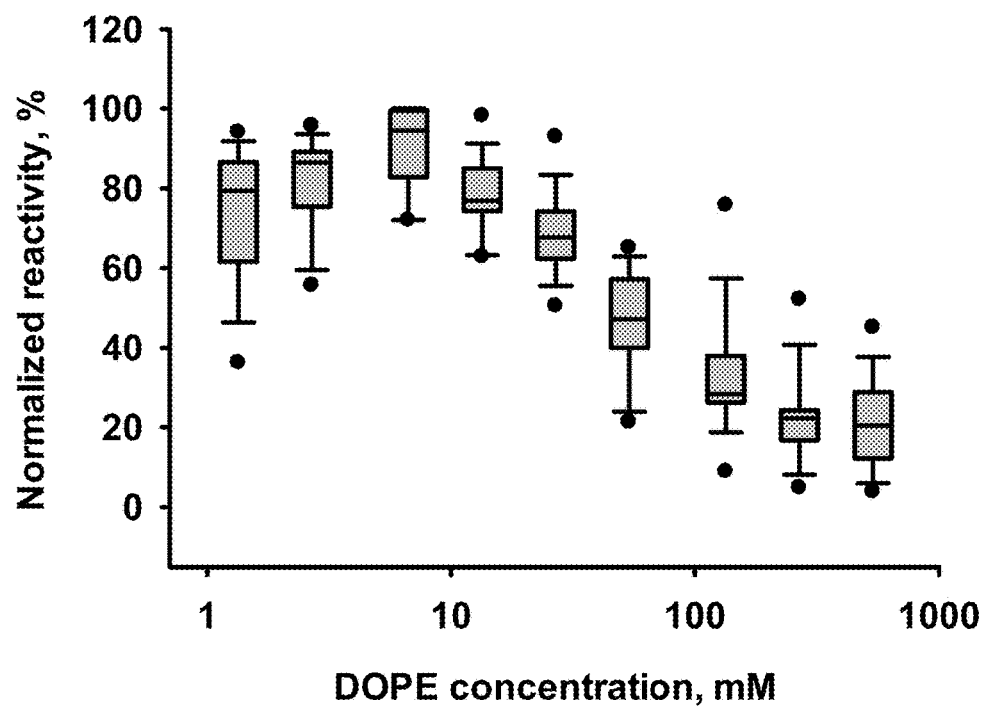
Figure 3:
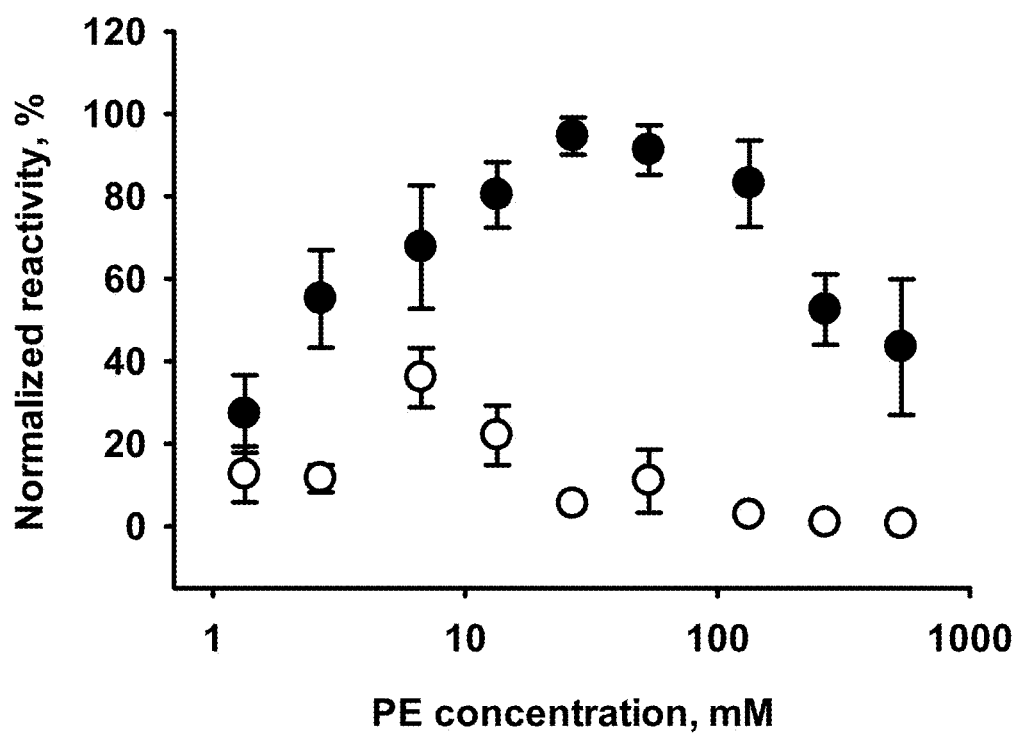
FIG. 3. Normalized aPE reactivities with increasing PE concentrations in the absence (o) or presence (•) of ABP. Data are mean±SD, n=3.

Among the 24 serum samples tested, 13 of them were cofactor-dependent which required ABP to achieve optimum ELISA readouts. Besides such a difference in ELISA procedure, these two types of serum samples also showed differences in the plot of normalized aPE reactivities versus PE concentrations (FIG. 2). Comparatively, cofactor-dependent samples required a greater antigen concentration to achieve appreciable signal levels. For example, 1 µg/ml PE hardly resulted in a detectable reactivity with cofactor-dependent aPE samples (FIGS. 2A and B); whereas independent samples already showed a decent level of reactivity (FIGS. 2C and D). It became apparent that there is a difference between dependent and independent samples in the antigen concentration required to achieve maximal aPE reactivity: the concentration of PE for plasma protein dependent serum was within a board range from about 20 to 100 µg/ml (FIGS. 2A and B); whereas the concentration of PE for independent samples to reach maximum readouts fell in a much narrower range around 5 µg/ml (FIGS. 2C and D). For cofactor-dependent samples, adding ABP in ELISA not only enhanced the reactivity with PE, but also right shifted the curve of normalized aPE reactivities versus PE concentrations. FIG. 3 showed a representative curve of normalized aPE reactivities with increasing PE concentrations for ELISA in the absence or presence of ABP.

Figure 4A:
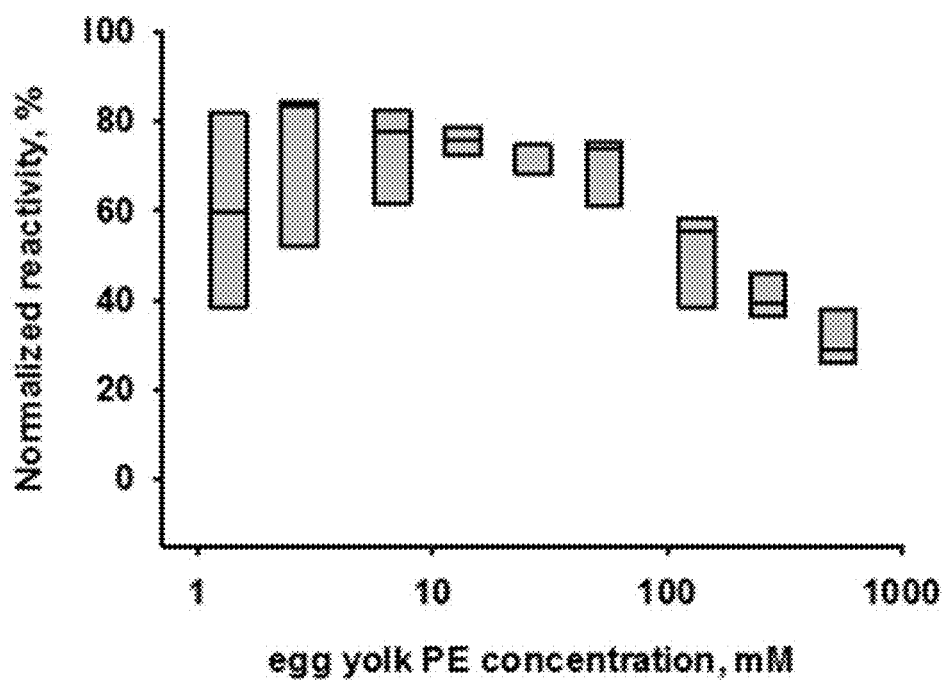
FIGS. 4A-D. Box plot of normalized cofactor-independent aPE reactivities with increasing egg yolk PE (A and C) or DOPE (B and D) concentrations for IgG (A and B, n=3) and IgM (C and D, n=8) isotypes. The box gives the $25^{th}$ to $75^{th}$ percentiles, with the median given by the line inside the box. Whiskers above and below the box indicate the $10^{th}$ and $90^{th}$ percentiles, with outliers marked by solid dots.
Figure 4B:
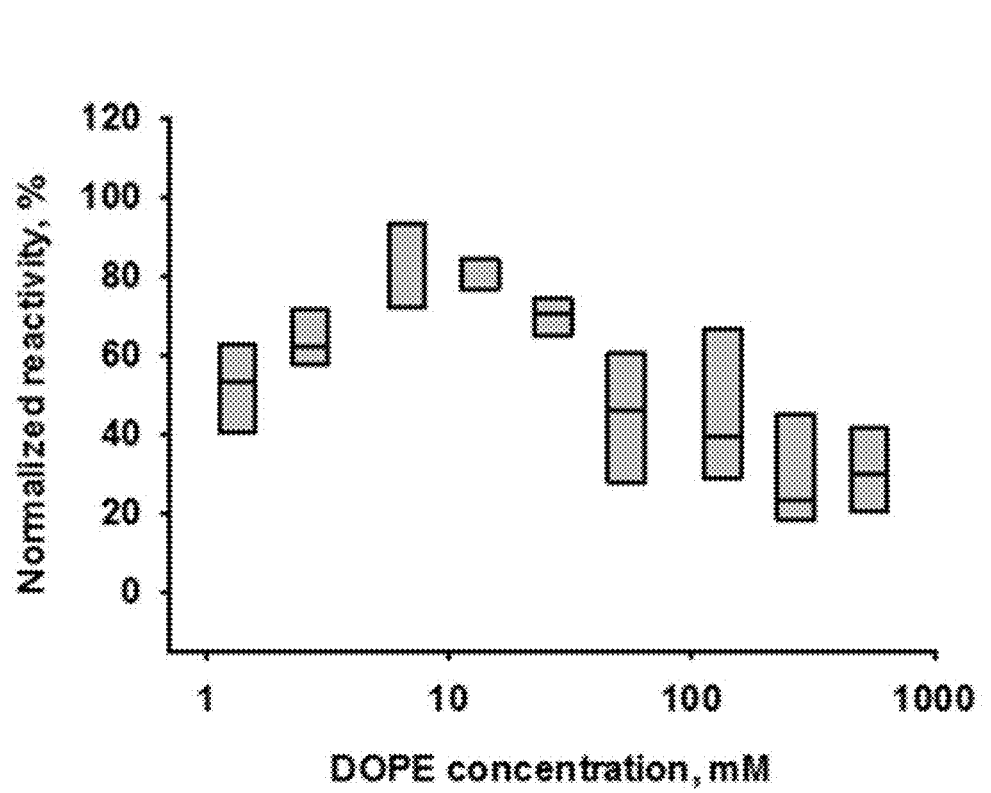
Figure 4C:
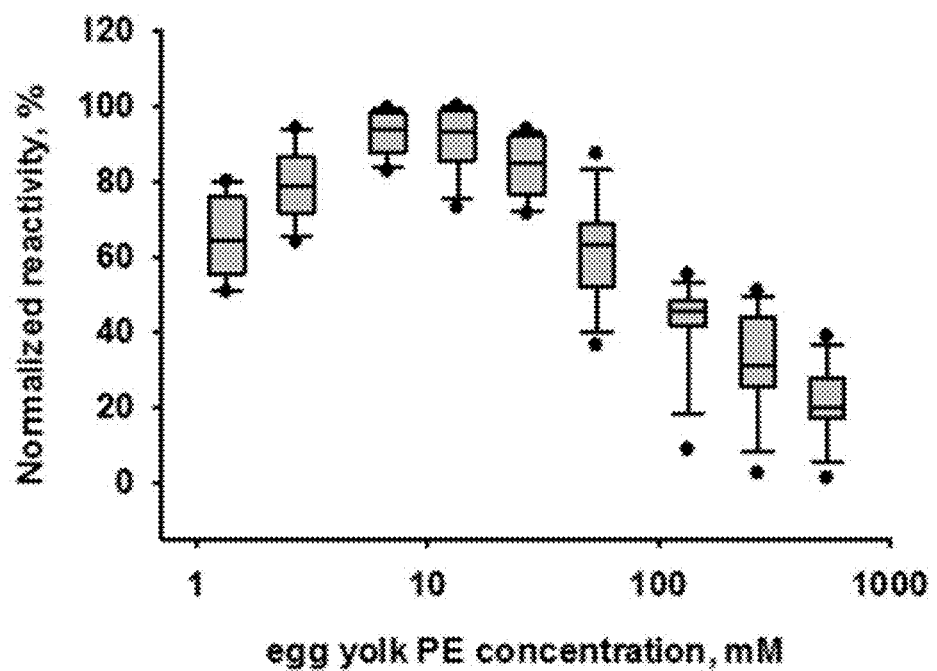
Figure 4D:
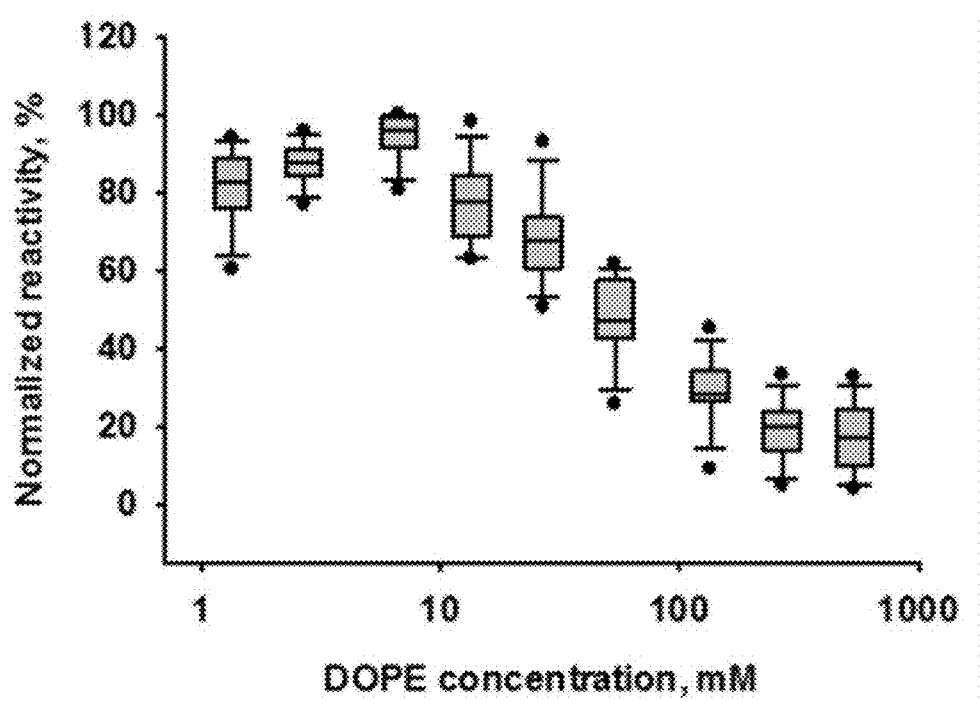
Figure 5A:
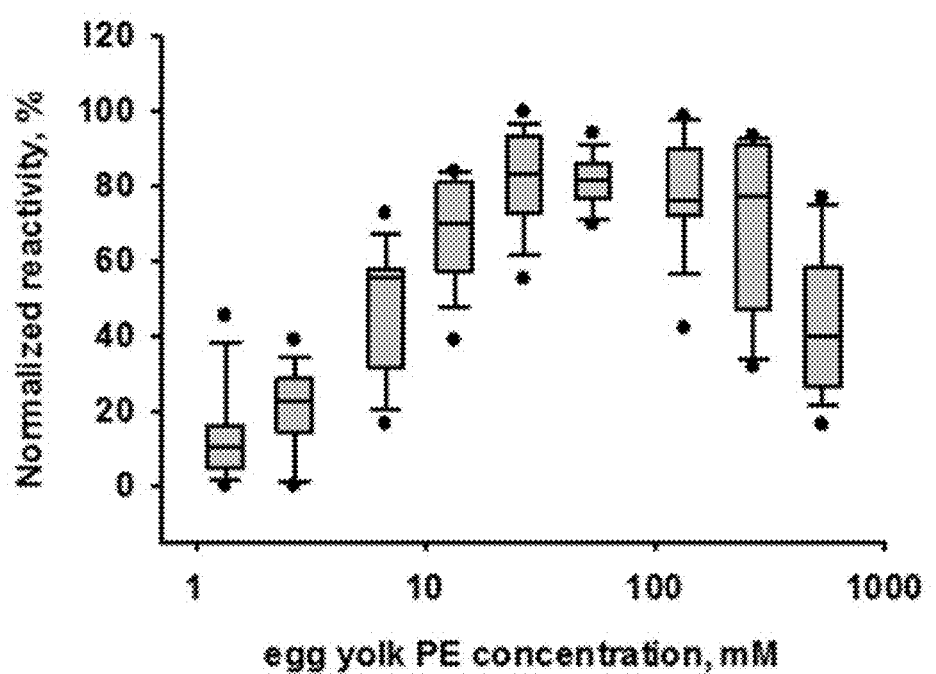
FIGS. 5A-D. Box plot of cofactor-dependent aPE reactivities with increasing concentrations of either egg yolk PE (A and C) or DOPE (B and D) for IgG (A and B, n=10) and IgM (C and D, n=3). The box gives the $25^{th}$ to $75^{th}$ percentiles, with the median given by the line inside the box. Whiskers above and below the box indicate the $10^{th}$ and $90^{th}$ percentiles, with outliers marked by solid dots.
Figure 5B:
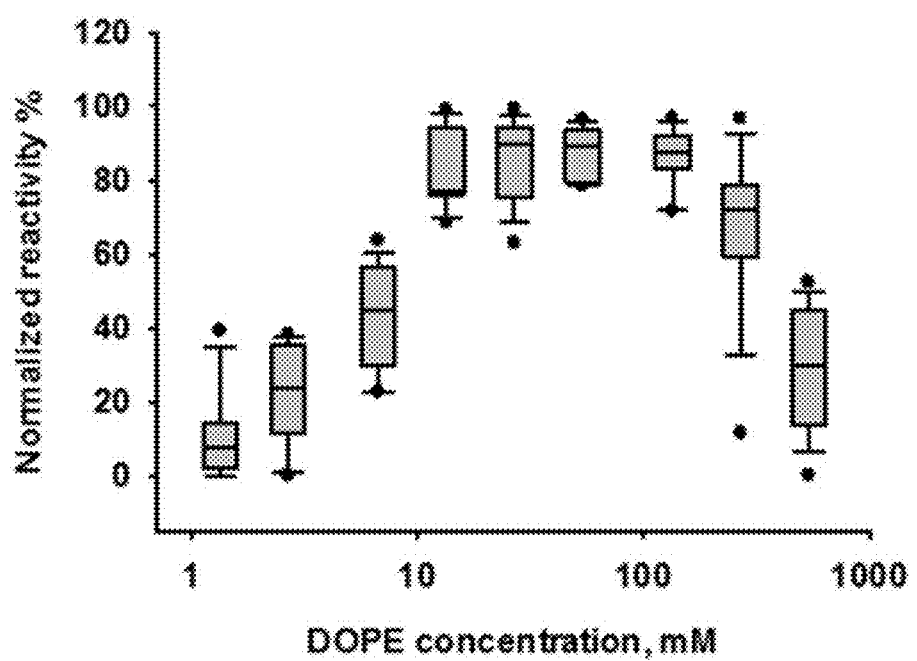
Figure 5C:
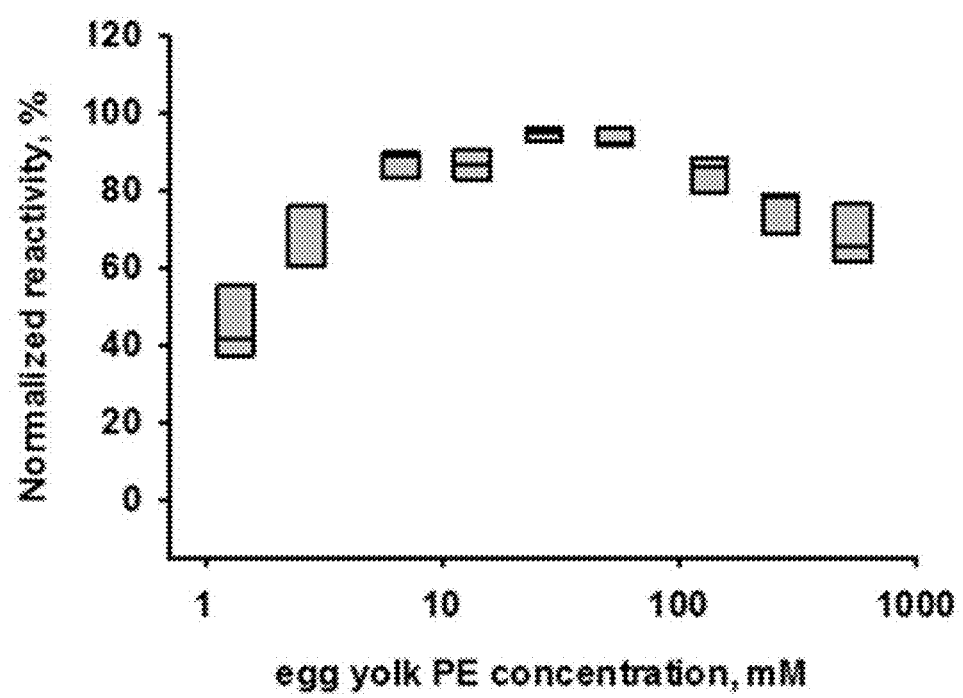
Figure 5D:
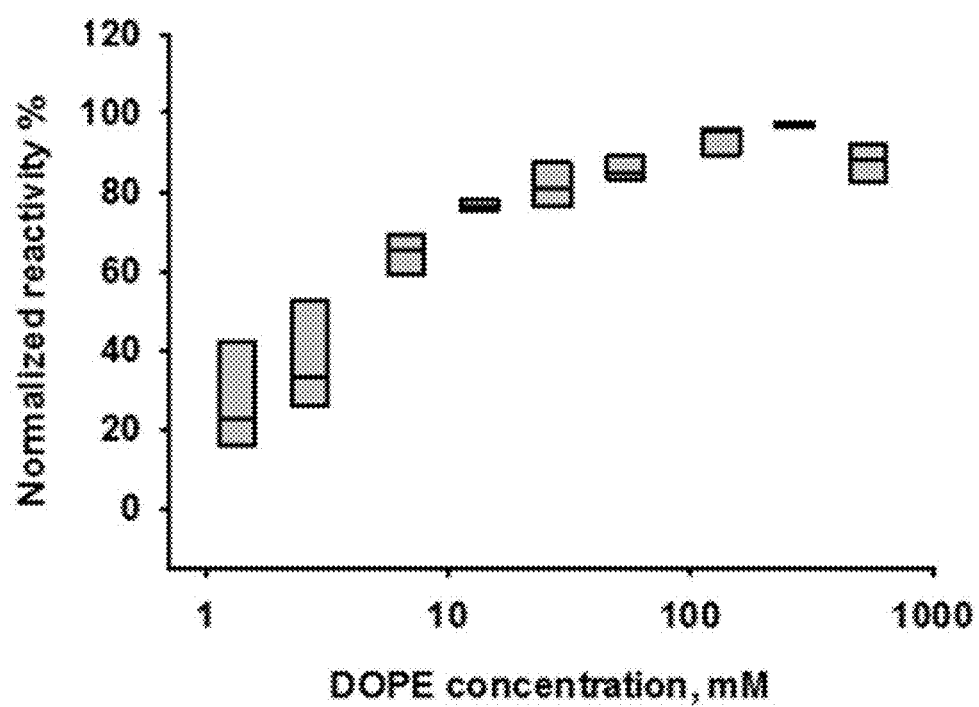

Different antibody isotypes did not result in significant variations in the optimal range of PE concentrations for ELISA readout. More specifically, cofactor-independent aPE serum samples consisted of 3 IgG and 8 IgM isotypes. When ELISA reactivity as a function of PE concentration is plotted based on individual isotypes (e.g., IgG versus IgM), the optimal range was consistent between the two isotypes (FIG. 4A vs. 4C, 4B vs. 4D). For cofactor-dependent samples, there were 10 IgG and 3 IgM isotypes. Again, the optimal PE concentration for ELISA readout was comparable between the two isotypes (FIG. 5A vs. 5C, 5B vs. 5D).

Influence of PE Composition (Expressed at Mol %) on aPE Detection

Figure 6:
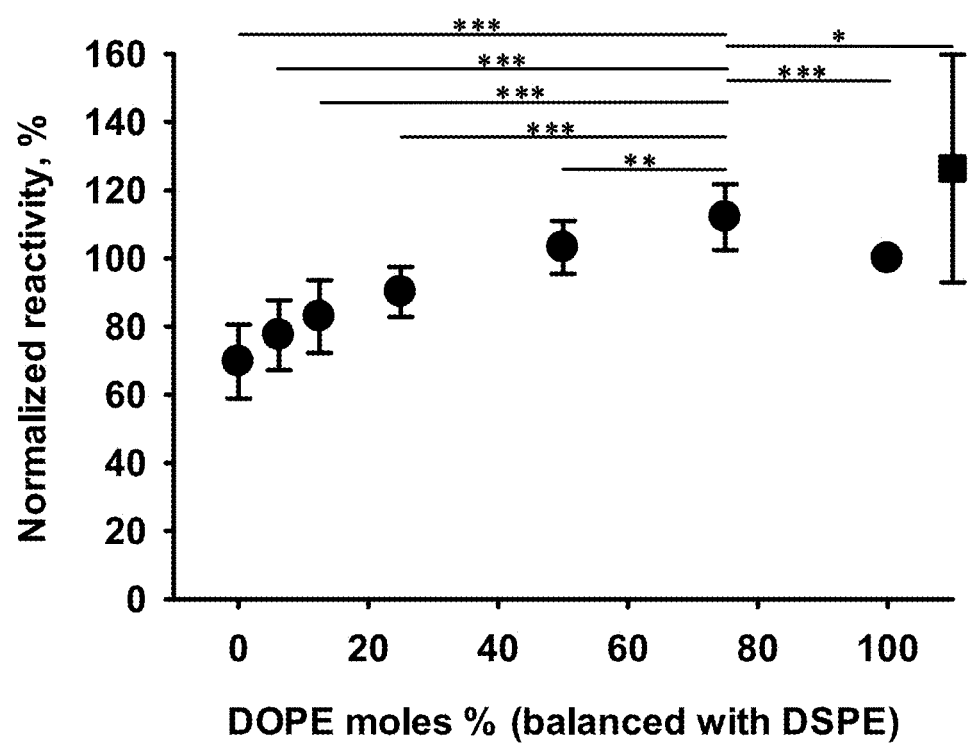
FIG. 6. Normalized aPE reactivities for binary DOPE/DSPE mixtures (•) and egg yolk PE (■). aPE reactivities were measured using 5 µg/ml egg yolk PE or equal molar amount of PE containing binary mixtures of DOPE and DSPE. aPE reactivities with different PE compositions were normalized to aPE reactivities with 100% DOPE. Data are mean±SD, n=4. * indicates p<0.5.  indicates p<0.05, and * indicates p<0.005.

When DOPE alone was compared with egg yolk PE, as shown in FIG. 1, PE origin does not appear to influence the dependence of aPE readouts as a function of PE concentrations. However, the absolute OD value obtained at 5 µg/ml egg yolk PE was higher than the value at same molar concentration of DOPE (FIG. 6). According to existing literature on phospholipid analysis, egg yolk PE consists of different species of PE molecules, including about 60% saturated and 40% unsaturated PE. The length of fatty acid chain also varies, with around 20% $C_{16}$, 60% $C_{18}$, 10% $C_{20}$, and 10% $C_{22}$ (ref. 17; herein incorporated by reference in its entirety). As shown in FIG. 6, by adding different percentages of DSPE into DOPE, aPE reactivities are modulated in a composition-dependent fashion. The lipid compositions of 75% DOPE and 25% DSPE, or 50% DOPE and 50% DSPE show an increased reactivity compared to 100% DOPE, raising the likelihood that the antigen PE from natural sources, such as the egg, can eventually be substituted with synthetic lipid compositions that can ensure consistency and optimized ELISA readouts.

Figure 7:
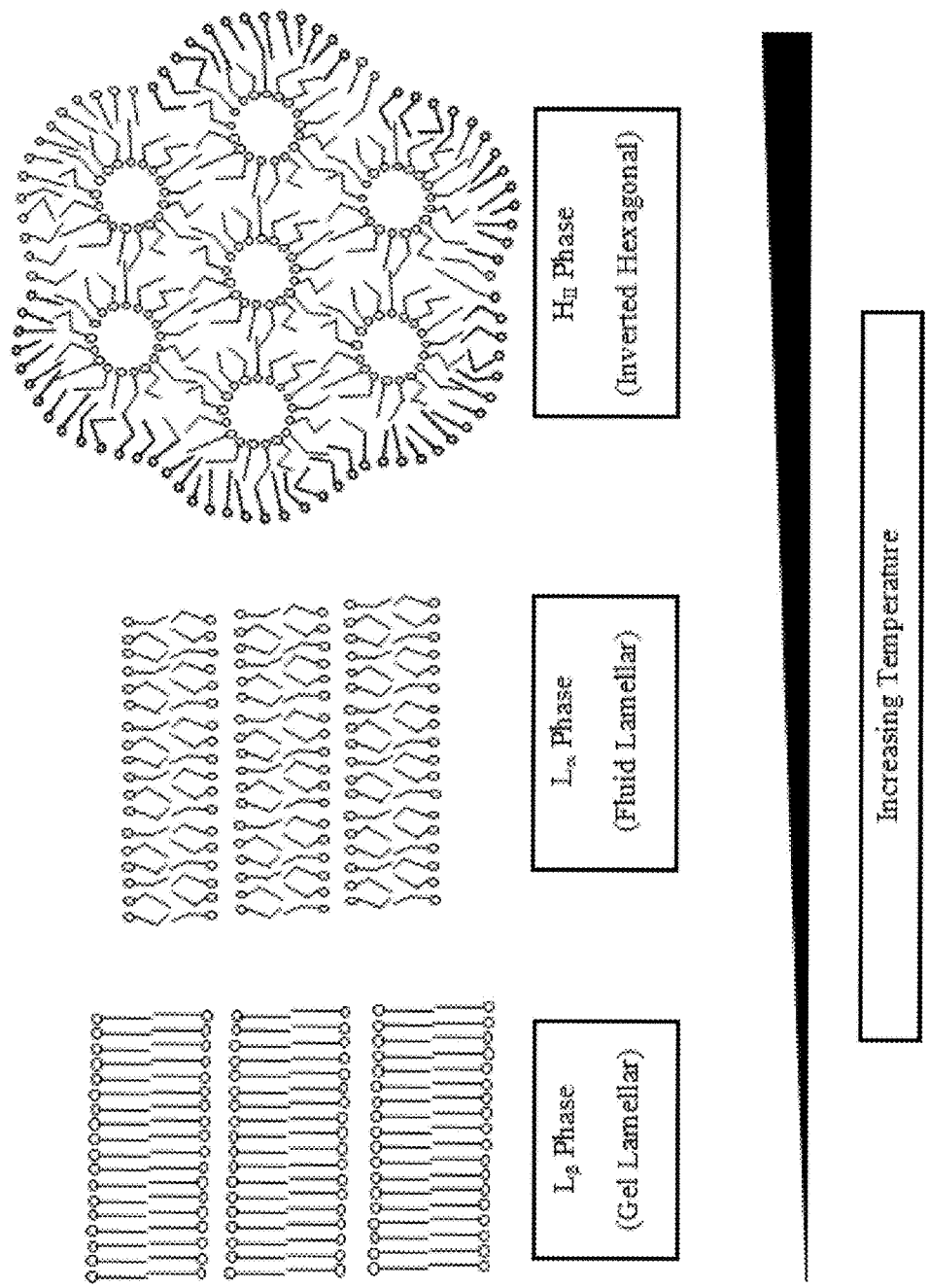
FIG. 7. A diagram showing distinct physical phases of lipids. In the lamellar phases, the lipid sheets stack to form multilamellar vesicles. In the inverted hexagonal phase, multiple cylinders of lipids stack, and are surrounded by a bounding monolayer in order to keep the hydrophobic tails away from aqueous environment.
Figure 8:
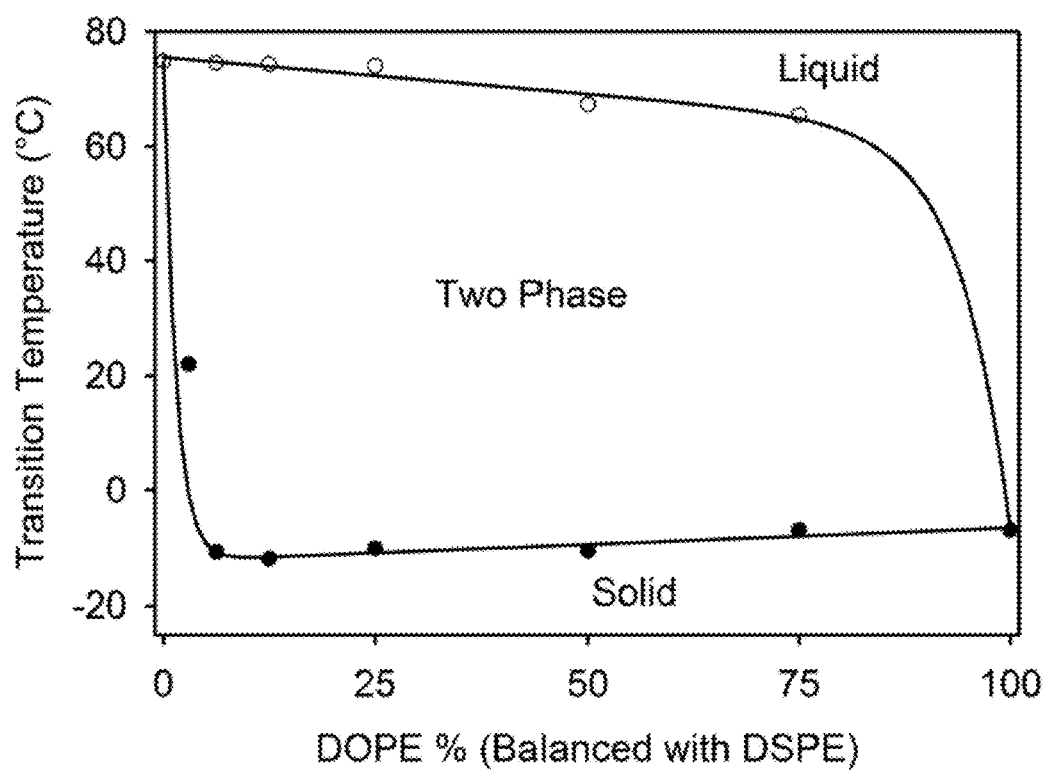
FIG. 8. Phase diagram for DOPE/DSPE mixtures. The transitions between the solid and the two phase region (filled symbols) and the two phase and the liquid region (open symbols) were measured by DSC (differential scanning calorimetry). Uncertainties are comparable to the symbol size. Solid lines indicate the phase boundaries suggested by the data.

Phase analysis was conducted to characterize the physical properties of the two-component lipid mixture. PE lipids, or lipids with PE head groups, typically form the phases illustrated and described in FIG. 7. At lower temperatures, a frozen or gel lamellar ($L_\beta$) phase is formed. At intermediate temperatures, the fluid lamellar ($L_\alpha$) phase is present and at elevated temperatures the lipids form the non-lamellar $H_{II}$ phase. The temperatures at which these phases occur depend decisively on the tail structure (18). DOPE (dioleoyl PE) has two identical monounsaturated tails and an $L_\alpha$-$H_{II}$ phase transition of 3° C. (19). DSPE (distearoyl PE) has two identical saturated tails; DSPE has an $L_\alpha$-$H_{II}$ phase transition of 100° C. Egg PE generally exhibits a $L_\beta$-$L_\alpha$ transition around 5° C. and a $L_\alpha$-$H_{II}$ transition at around 30° C. (20). A single lipid system at equilibrium generally forms only one phase at a given temperature; systems composed of two lipids at equilibrium can form two phases at a given temperature. The phase diagram for DOPE/DSPE mixtures at 6.25, 12.5, 25, 50, 17 and 100% DOPE balanced with DSPE is shown in FIG. 8. At higher temperatures, around or above the melting temperature of DSPE, the lipid mixtures form a fluid phase; at lower temperatures, around or below the melting temperature of DOPE, the lipid mixtures form solid phases. In between these extremes, they phase separate into a solid, DSPE rich phase and a liquid, DOPE rich phase.

A trend is that DSPE rich mixtures have lower reactivities than DOPE rich mixtures. It is contemplated that the fluid nature of DOPE at the temperature at which the ELISA assays were conducted made DOPE more reactive with the aPE. However, as pure DOPE goes to the inverted hexagonal phase, the apparent drop in reactivity may be due to the fact that most of the DOPE forms cylinders that might be inaccessible to the aPE, leaving only the bounding monolayer available to interact with the aPE (FIG. 8). As such, the data demonstrated that aPE ELISA reactivities can be modulated by adjusting the physical forms of lipid mixture, and that the ELISA data were consistent with phase measurements using DSC.

Example 2

Synthetic Antigen Compositions for Detecting Antiphosphatidylethanolamine

In order to achieve consistent and optimized ELISA performance for aPE testing, different preparations of synthetic PE species were investigated to identify defined combinations of PE that outperform PE obtained from natural sources such as the egg yolk, animal brain, bacteria, etc. PE products from natural sources are known to vary in quality and compositions depending on the vendors and batches. Synthetic PE species (16:0 PE, 18:0 PE, 18:1 PE, 20:4 PE and 22:6 PE) were purchased from commercial sources (Avanti Polar Lipids). These are PE species that are commercially available as individual chemically defined products, and are representative among many species of PE. Using individual or combinations of the above 5 common PE species, substituting natural PE using defined and optimized PE compositions is demonstrated herein.

Figure 9:
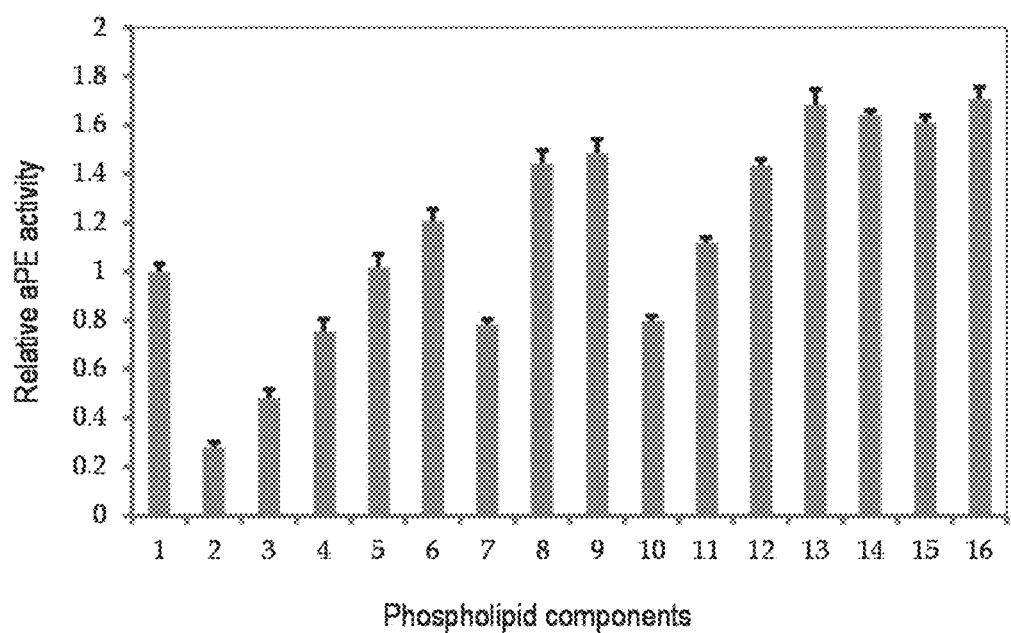
FIG. 9. Graph depicting relative aPE activities for various PE combinations: 1, Egg PE; 2, 16:0 PE; 3, 18:0 PE; 4, 18:1 PE; 5, 20:4 PE; 6, 22:6 PE; 7, 30% 16:0 PE and 70% 18:1PE; 8, 30% 16:0 PE and 70% 20:4 PE; 9, 30% 16:0 PE and 70% 22:6 PE; 10, 30% 18:0 PE and 70% 18:1PE; 11, 30% 18:0 PE and 70% 20:4 PE; 12, 30% 18:0 PE and 70% 22:6 PE; 13, 15% 16:0 PE, 15% 18:0 PE, 17.5% 18:1 PE and 52.5% 20:4 PE; 14, 15% 16:0 PE, 15% 18:0 PE, 23.3% 18:1 PE and 46.7% 20:4 PE; 15, 20% 16:0 PE, 10% 18:0 PE, 15.75% 18:1 PE, 47.25% 20:4 PE; and 7% 22:6 PE; 16, 20% 16:0 PE, 10% 18:0 PE, 21% 18:1 PE and 42% 20:4 PE and 7% 22:6 PE. 0.5 mg indicated PE was coated on each well of 96 plate, $OD_{405}$ was measured after Elisa and the relative OD value was deducted the normal human serum value and normalized with egg PE value. The error bar represents SEM. n=3. serum was from patient J083006H.

The Effect and Optimization of Synthetic Phospholipid Compositions on the ELISA Performance of Cofactor Independent IgM aPE ELISA data using one of these 5 PE species or different PE combinations to detect cofactor-independent aPE IgM reactivity in human patient serum samples is shown in FIG. 9. The results demonstrate that each of the unsaturated PE species had better performance than the corresponding saturated PE species that had equal fatty acid length (FIG. 9, formulations 3 versus 4). Also, PE species with longer fatty acid tails with a greater degree of unsaturation (for example 20:4 PE and 22:6 PE) tends to have better performance than shorter ones with a lower degree of unsaturation (FIG. 9, formulations 2-6). Comparatively, the single PE species with shorter fatty acid tails and a lower degree of unsaturation had inferior performance than egg PE (FIG. 9, formulations 2-4); however, single PE species with longer fatty acid tails and a greater degree of unsaturation could out-perform egg PE (FIG. 9, formulations 5 and 6). Egg PE is currently the most widely used source of PE in ELISA tests for aPE. Additionally, the combinations of one saturated and one unsaturated PE species can have a stronger performance than either one of the two individually (FIG. 9, formulation 7 versus 2 and 3; formulation 8 versus 2 and 5; formulation 9 versus 2 and 6; formulation 10 versus 3 and 4; formulation 11 versus 3 and 5, formulation 12 versus 3 and 6). The compositions of two PE species, with one saturated and one unsaturated, can out-perform egg PE when the unsaturated PE species contains longer fatty acid tails with a greater degrees of unsaturation (FIG. 9, formulations 8, 9, 11 and 12). Furthermore, a combination of a greater variety of PE species, four or five species, tends to have even higher performance (FIG. 9, formulations 13-16), being better than single PE species and combinations of two PE species, and decidedly superior than egg PE.

ELISA performance of different PE compositions was examined by varying the contents of saturated PE species from 0 to 80%. It was determined that a higher ELISA performance was achieved when the content of saturated PE species was relatively low, between 0 to 40% (FIG. 10, formulation 2-6, 9-13), where these formulations significantly and consistently out-performed egg PE. When the percentage of saturated PE species was too high (FIG. 10, formulations 7-8, 14-15), it was accompanied with diminished ELISA performance.

Figure 10:
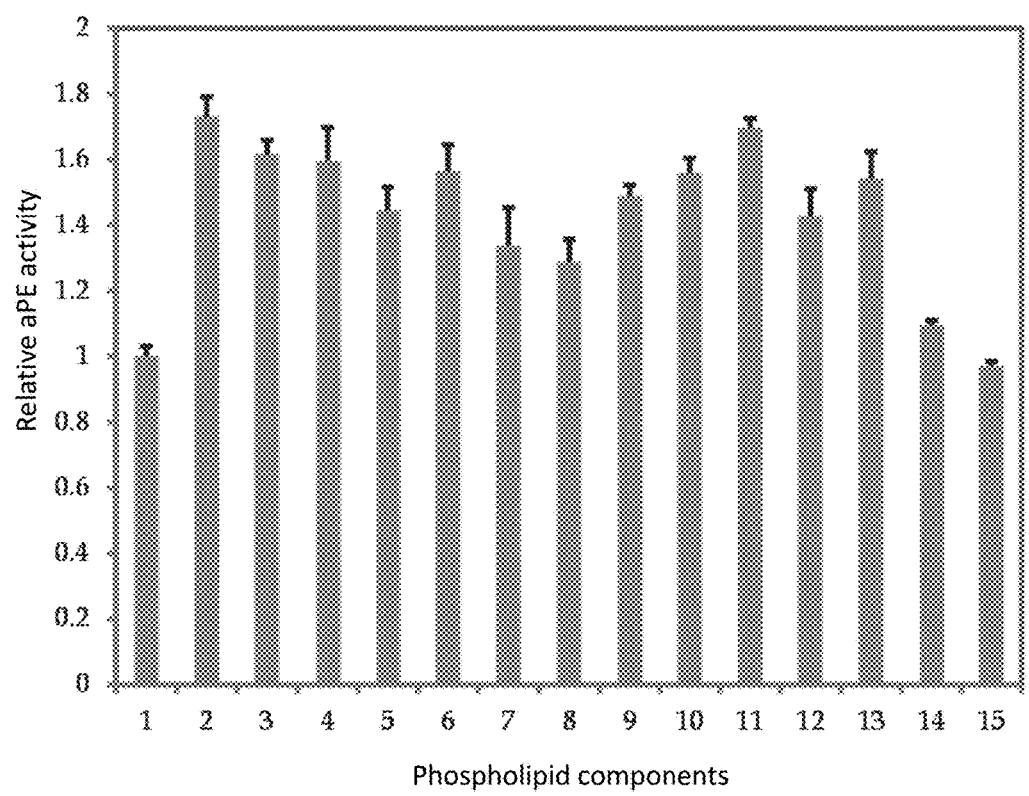
FIG. 10. Graph depicting screening of phospholipid combinations to detect IgM aPE activity. 1, egg PE; 2, 0% 18:0 PE, 16.6% 18:1 PE, 33.2% 20:4 PE, and 49.8% 22:6 PE; 3, 10% 18:0 PE, 15% 18:1 PE, 30% 20:4 PE, and 45% 22:6 PE; 4, 20% 18:0 PE, 13.3% 18:1 PE, 26.6% 20:4 PE, and 39.9% 22:6 PE; 5, 30% 18:0 PE, 11.6% 18:1 PE, 23.2% 20:4 PE, and 34.8% 22:6 PE; 6, 40% 18:0 PE, 10% 18:1 PE, 20% 20:4 PE, and 30% 22:6 PE; 7, 60% 18:0 PE, 6.6% 18:1 PE, 13.2% 20:4 PE, and 19.8% 22:6 PE; 8, 80%, 18:0 PE, 3.3% 18:1 PE, 6.6% 20:4 PE, and 9.9% 22:6 PE; 9, 0% 18:0 PE, 16.6%, 18:1 PE, 49.8% 20:4 PE, and 33.2% 22:6 PE; 10, 10% 18:0 PE, 15% 18:1 PE, 45% 20:4 PE, and 30% 22:6 PE; 11, 20% 18:0 PE, 13.3% 18:1 PE, 39.9% 20:4 PE, and 26.6% 22:6 PE; 12, 30% 18:0 PE, 11.6% 18:1 PE, 34.8% 20:4 PE, and 23.2% 22:6 PE; 13, 40% 18:0 PE, 10% 18:1 PE, 30% 20:4 PE, and 20% 22:6 PE; 14, 60% 18:0 PE, 13.2% 18:1 PE, 6.6% 20:4 PE, and 19.8% 22:6 PE; 15, 80% 18:0 PE, 3.3% 18:1 PE, 9.9% 20:4 PE, and 6.6% 22:6 PE. 0.5 mg indicated PE was coated on each well of 96 plate, $OD_{405}$ was measured after Elisa and the relative OD value was deducted the normal human serum value and normalized with egg PE value. The error bar represents SEM. n=3
Figure 11:
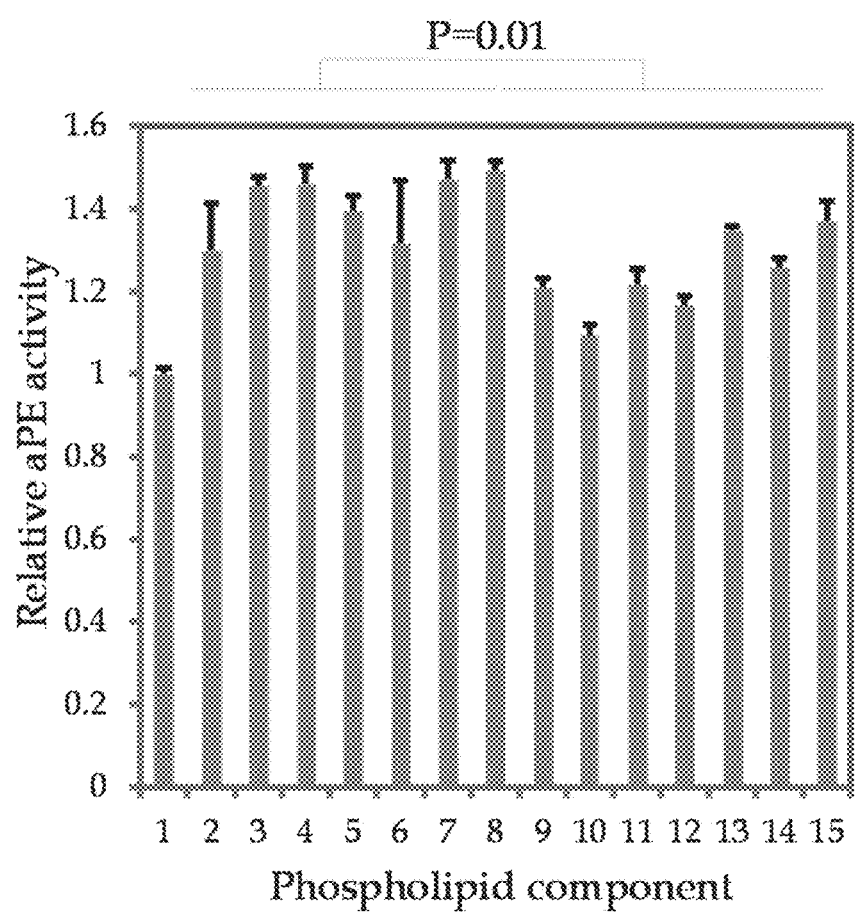
FIG. 11. Determination of three unsaturated PE ratio in components. 1, egg PE; 2, 20% 18:0 PE, 33.3% 18:1 PE, 33.3% 20:4 PE, and 33.3% 22:6 PE; 3, 20% 18:0 PE, 20% 18:1 PE, 60% 20:4 PE, and 0% 22:6 PE; 4, 20% 18:0 PE, 20% 18:1 PE, 0% 20:4 PE, and 60% 22:6 PE; 5, 20% 18:0 PE, 13.3% 18:1 PE, 66.5% 20:4 PE, and 0% 22:6 PE; 6, 20% 18:0 PE, 13.3% 18:1 PE, 0% 20:4 PE, and 66.5% 22:6 PE; 7, 20% 18:0 PE, 13.3% 18:1 PE, 26.6% 20:4 PE, and 39.9% 22:6 PE; 8, 20% 18:0 PE, 13.3% 18:1 PE, 39.9% 20:4 PE, and 26.6% 22:6 PE; 9, 10% 18:0 PE, 30% 18:1 PE, 30% 20:4 PE, and 30% 22:6 PE; 10, 10% 18:0 PE, 22.5% 18:1

Based on the data in FIG. 10, the saturated PE species in the formulation was fixed at 20% or 10%, and investigated the impact of variations among the remaining unsaturated PE species (FIG. 11). In these studies, the content of unsaturated PE species, which accounted for 80 or 90% of the formulations, were varied so that the ratios among 18:1 PE, 20:4 PE and 22:6 PE were 1:1:1, 1:3:0, 1:0:3, 1:5:0, 1:0:5, 1:2:3, and 1:3:2 (FIG. 11, formulations 2-8 and 9-15 for 20% or 10% of saturated PE species, respectively). For these studies, we determined that overall, the formulations with 20% saturated PE species were generally superior to 10% PE, and that variations in the ratios among the unsaturated PE species did not have a dramatic impact on ELISA performance.

Based on the results in FIG. 11, after selecting a formulation (20% 18:0 PE, 13.3% 18:1 PE, 39.9% 20:4 PE, and 26.6% 22:6 PE) among the candidates that gave similarly optimized ELISA performance, the impact of the amount of coating material on ELISA performance was tested. As shown in FIG. 12B, the optimal amount of coating was in the range from 0.25 to 1 µg per well in a 96 well ELISA plate. When the coating material was too little (0.125 µg per well) or too much (2 µg per well or greater), it tended to adversely affect the ELISA performance.

After selecting an optimal synthetic PE composition as a kit formulation, a head-to-head comparison of the ELISA performance with egg PE was conducted using 11 cofactor-independent aPE IgM patient serum samples. As shown in FIG. 13, the synthetic formulation (20% 18:0 PE, 13.3% 18:1 PE, 39.9% 20:4 PE, and 26.6% 22:6 PE) consistently and significantly out-performed egg PE in ELISA (P=0.006, n=11). In multiple cases, the readout of the ELISA was improved up to 400%. These improvements will reduce the chance of false-negative detection and provide a more reliable diagnostic test.

The Effect and Optimization of Synthetic Phospholipid Compositions on the ELISA Performance of Cofactor Independent IgG aPE FIG. 14 demonstrates relative ELISA performance against egg PE from single and combinations of synthetic PE species for detecting cofactor-independent aPE IgG reactivity. The results indicate that for a representative aPE serum sample, the single 20:4 PE (FIG. 14, formulation 5) had the highest OD value, which was nearly 14 folds greater than egg PI on a representative patient serum sample. Many other formulations of synthetic PE (FIG. 14, formulations 4, 6, 7, 11, 13, 14, 15 and 16) also significantly out-performed egg PE. It appeared that when the combination contains a higher percentage of 20:4 PE, it had a greater tendency to result in better sensitivity than egg PE, which indicated 20:4 PE may be an important component in the PE formulations. The inclusion of PE species with longer fatty acid tails with a greater degree of unsaturation (for example 22:6 PE) also appeared to result in improved ELISA results compared to egg PE.

Based on these results, a head-to-head study between the 20:4 PE and egg PE for detecting the aPE reactivity was conducted among 14 cofactor-independent IgG patient serum samples (FIG. 15). The data indicated that most of patient serum samples having high aPE reactivity on egg PE had even stronger aPE reactivity on 20:4 PE, with some samples were improved by 500% or more. Certain patient samples that were negative or marginally positive by egg PE showed strongly positive reactivity to 20:4 PE. Samples that were negative by 20:4 PE were also negative by egg PE. Overall, the formulation of 20:4 PE out-performed egg PE significantly with P=0.012 (n=14).

The Effect and Optimization of Synthetic Phospholipid Compositions on the ELISA Performance of Cofactor-Dependent aPE Screening studies were conducted using different synthetic PE compositions on the ELISA performance for cofactor-dependent aPE. FIGS. 16A and B demonstrated OD values from representative cofactor-dependent aPE IgA and IgG, respectively. The data indicated that a single species of 18:1 PE (FIGS. 16A and B, formulation 4) was the best candidate, and that there was no significance difference with egg PE. In addition, the inclusion of a higher percentage of 18:1 PE, or PE species that have longer fatty acid tails with a greater degree of unsaturation (for example, 20:4 PE and 22:6 PE), results in a higher OD value.

In a head-to-head comparison with egg PE, 18:1 PE to test for detecting cofactor-dependent aPE reactivity of 12 patient serum samples, which included 3 IgM aPE, 8 IgG aPE and 1 IgA aPE. The results (FIG. 17) indicated that 18:1 PE delivered similar sensitivity as egg PE for detecting aPE reactivity, with a P value of 0.99. While there was no significant difference between egg PE and 18:1 PE in terms of performance, the latter has the advantage of being a chemically defined composition, which helps eliminate uncertainties associated with natural PE sources that can vary from different vendors and batches, as such the defined composition is expected to perform more consistently with a greater potential for wide adaptation in practice.

Testing ELISA Performance with Synthetic PE Species by using Purified Total IgG

To minimize uncertainties caused by potential confounding factors in the serum and variations in immunoglobulin contents, the total IgG was isolated from representative aPE patient serum samples and was used to validate ELISA assays.

Microplates were coated using Egg PE, 20:4 PE or 18:1 PE for IgG aPE ELISA for normal human serum, a representative cofactor-dependent and cofactor-independent patient serum. As shown in FIG. 18, the cofactor-independent sample had significant reactivity against egg PE and 20:4 PE, whereas the signal from 18:1 PE was near negligible. In contrast, for the cofactor-dependent sample, there was apparent reactivity against egg PE and 18:1 PE, but not 20:4 PE. To validate the difference in reactivity between 18:1 PE and 20:4 PE in cofactor-dependent aPE, total IgG from two other cofactor-dependent aPE samples were isolated, and their reactivity against egg PE, 20:4 PE, 18:1 PE and PS as a negative control was tested. The ELISA results (FIG. 19) indicated that again, the cofactor-dependent aPE IgG sample strongly recognized egg PE and 18:1 PE, but not 20:4 PE or the negative control PS. These findings were consistent with 20:4 PE being a preferred antigen for cofactor-independent IgG aPE, and that 18:1 PE is a preferred antigen for cofactor-dependent IgG aPE. Additionally, the presence of ABP significantly diminished the reactivity of cofactor-independent aPE, indicating that ABP may contain elements that potentially compete with cofactor-independent aPE.

REFERENCES

The following references, some of which are cited above, are herein incorporated by reference in their entireties.

1. Harris E N. 1987. Syndrome of the black swan. Br J Rheumatol 26(5):324-326.
2. Wilson W A, Gharavi A E, Koike T, Lockshin M D, Branch D W, Piette J C, Brey R, Derksen R, Harris E N, Hughes G R, Triplett D A, Khamashta M A. 1999. International consensus statement on preliminary classification criteria for definite antiphospholipid syndrome: report of an international workshop. Arthritis Rheum 42(7):1309-1311.
3. Miyakis S, Lockshin M D, Atsumi T, Branch D W, Brey R L, Cervera R, Derksen R H, P G DEG, Koike T, Meroni P L, Reber G, Shoenfeld Y, Tincani A, Vlachoyiannopoulos P G, Krilis S A. 2006. International consensus statement on an update of the classification criteria for definite antiphospholipid syndrome (APS). J Thromb Haemost 4(2):295-306.
4. Rodriguez-Garcia J L, Bertolaccini M L, Cuadrado M J, Sanna G, Ateka-Barrutia O, Khamashta M A. 2012. Clinical manifestations of antiphospholipid syndrome (APS) with and without antiphospholipid antibodies (the so-called 'seronegative APS'). Ann Rheum Dis 71(2): 242-244.
5. Nayfe R, Uthman I, Aoun J, Saad Aldin E, Merashli M, Khamashta M A. 2013. Seronegative antiphospholipid syndrome. Rheumatology (Oxford) 52(8):1358-1367.
6. Sugi T, Matsubayashi H, Inomo A, Dan L, Makino T. 2004. Antiphosphatidylethanolamine antibodies in recurrent early pregnancy loss and mid-to-late pregnancy loss. J Obstet Gynaecol Res 30(4):326-332.
7. Sanmarco M, Gayet S, Alessi M C, Audrain M, de Maistre E, Gris J C, de Groot P G, Hachulla E, Harle J R, Sie P, Boffa M C. 2007. Antiphosphatidylethanolamine antibodies are associated with an increased odds ratio for thrombosis. A multicenter study with the participation of the European Forum on antiphospholipid antibodies. Thromb Haemost 97(6):949-954.
8. Staub H L, Bertolaccini M L, Khamashta M A. 2012. Anti-phosphatidylethanolamine antibody, thromboembolic events and the antiphospholipid syndrome. Autoimmun Rev 12(2):230-234.
9. Staub H L, Harris E N, Khamashta M A, Savidge G, Chahade W H, Hughes G R. 1989. Antibody to phosphatidylethanolamine in a patient with lupus anticoagulant and thrombosis. Ann Rheum Dis 48(2):166-169.
10. Karmochkine M, Cacoub P, Piette J C, Godeau P, Boffa M C. 1992. Antiphosphatidylethanolamine antibody as the sole antiphospholipid antibody in systemic lupus erythematosus with thrombosis. Clin Exp Rheumatol 10(6):603-605.
11. Berard M, Chantome R, Marcelli A, Boffa M C. 1996. Antiphosphatidylethanolamine antibodies as the only antiphospholipid antibodies. I. Association with thrombosis and vascular cutaneous diseases. J Rheumatol 23(8): 1369-1374.
12. Boffa M C, Berard M, Sugi T, McIntyre J A. 1996. Antiphosphatidylethanolamine antibodies as the only antiphospholipid antibodies detected by ELISA. II. Kininogen reactivity. J Rheumatol 23(8):1375-1379.
13. McIntyre J A, Wagenknecht D R. 2000. Anti-phosphatidylethanolamine (aPE) antibodies: a survey. J Autoimmun 15(2):185-193.
14. Sanmarco M. 2010. ELISA for antiphosphatidylethanolamine antibody detection: high impact of assay buffer on results. Journal of immunological methods 358(1-2):9-16.
15. Drouvalakis K A, Buchanan R R. 1999. Microtitre plate and assay buffer alter detection of antiphosphatidylethanolamine antibodies in lupus anticoagulant positive plasma. Thromb Res 94(4):205-212.
16. Bartlett G R. 1959. Phosphorus assay in column chromatography. J Biol Chem 234(3):466-468.
17. Hawke J C. 1959. The fatty acids of phosphatidylethanolamine and phosphatidylcholine from hen's egg. Biochem J 71(3):588-592.
18. Harper P E, Mannock D A, Lewis R N, McElhaney R N, Gruner S M. 2001. X-ray diffraction structures of some phosphatidylethanolamine lamellar and inverted hexagonal phases. Biophys J 81(5):2693-2706.
19. Toombes G E, Finnefrock A C, Tate M W, Gruner S M. 2002. Determination of L(alpha)-H(II) phase transition temperature for 1,2-dioleoyl-sn-glycero-3-phosphatidylethanolamine. Biophys J 82(5):2504-2510.
20. Cullis P R, de Kruijff B. 1978. The polymorphic phase behaviour of phosphatidylethanolamines of natural and synthetic origin. A 31P NMR study. Biochim Biophys Acta 513(1):31-42.

The invention claimed is:

1. A composition comprising a population of defined phosphatidylethanolamine (PE) species, comprising at least 10-30 mol % of PE composition of each of 18:1 PE, 20:4 PE, and 22:6 PE.

2. A composition comprising a population of defined phosphatidylethanolamine (PE) species, comprising 10-30 mol % 18:0 PE, 5-20 mol % 18:1 PE, 20-50 mol % 20:4 PE, and 15-40 mol % 22:6 PE.

3. The composition of claim 1, comprising about 20 mol % 18:0 PE, about 13.3 mol % 18:1, about 39.9 mol % 20:4 PE, and about 26.6 mol % 22:6 PE.

4. A method comprising exposing a sample suspected of comprising anti-phosphatidylethanolamine (aPE) antibodies to a composition of claim 1, and detecting the binding of the aPE antibodies to the PE species.

5. The method of claim 4, wherein the sample is a blood sample from a subject and/or a processed blood product.

6. The method of claim 4, wherein the method comprises performing an enzyme linked immunosorbent assay (ELISA).

7. The method of claim 6, wherein the ELISA is a sandwich ELISA or a competitive ELISA.

8. A system comprising a vessel having a composition of claim 1 contained within and/or coated onto a surface of the vessel.

9. The system of claim 8, wherein the vessel is a well of a multiwell plate, and the surface is a well-bottom and/or sidewall.

10. A kit for performing an immunoassay comprising a composition of claim 1 and additional reagents and/or materials for performing the immunoassay, the additional reagents and/or materials selected from the group consisting of buffer, controls, labeled secondary antibody, labeled aPE antibody, a microwell plate, software, and instructions.

* * * * *